United States Patent
Alexander et al.

(10) Patent No.: US 10,058,240 B2
(45) Date of Patent: Aug. 28, 2018

(54) SYSTEMS, IMPLANTS, TOOLS, AND METHODS FOR TREATMENTS OF PELVIC CONDITIONS

(75) Inventors: James A. Alexander, Excelsior, MN (US); Benjamin Y. Arcand, Minneapolis, MN (US); Justin H. Huelman, Lino Lakes, MN (US); Chaouki A. Khamis, Los Gatos, CA (US); Micah D. Thorson, North Branch, MN (US); William S. Tremulis, Redwood City, CA (US); Thomas O. Viker, New Brighton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 322 days.

(21) Appl. No.: 13/537,977

(22) Filed: Jun. 29, 2012
(Under 37 CFR 1.47)

(65) Prior Publication Data
US 2013/0006061 A1 Jan. 3, 2013

Related U.S. Application Data

(60) Provisional application No. 61/502,694, filed on Jun. 29, 2011.

(51) Int. Cl.
*A61B 1/32* (2006.01)
*A61B 1/06* (2006.01)
*A61B 1/303* (2006.01)

(52) U.S. Cl.
CPC .......... *A61B 1/0676* (2013.01); *A61B 1/0684* (2013.01); *A61B 1/303* (2013.01); *A61B 1/32* (2013.01)

(58) Field of Classification Search
CPC ................. A61B 1/303; A61B 2017/0225
USPC ................. 606/193, 198; 600/203, 218, 222
See application file for complete search history.

(56) References Cited

U.S. PATENT DOCUMENTS

| | | | |
|---|---|---|---|
| 2,738,790 | A | 3/1956 | Todt et al. |
| 3,124,136 | A | 3/1964 | Usher |
| 3,182,662 | A | 5/1965 | Shirodkar |
| 3,311,110 | A | 3/1967 | Singerman et al. |
| 3,384,073 | A | 5/1968 | Van Winkle, Jr. |
| 3,472,232 | A | 10/1969 | Earl |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS http://www.thefreedictionary.com, definition of "membrane", accessed Jan. 9, 2015.*

(Continued)

*Primary Examiner* — Jan Christopher Merene
(74) *Attorney, Agent, or Firm* — Brake Hughes Bellermann LLP

(57) ABSTRACT

Described are various embodiments of surgical procedure systems, devices, tools, and methods, useful for treating pelvic conditions such as vaginal prolapse and other conditions caused by muscle and ligament weakness, the devices and tools being useful for transvaginally accessing a posterior region of pelvic anatomy, and related methods.

10 Claims, 13 Drawing Sheets

(56) References Cited

U.S. PATENT DOCUMENTS

| | | | |
|---|---|---|---|
| 3,580,313 | A | 5/1971 | McKnight |
| 3,763,860 | A | 10/1973 | Clarke |
| 3,789,828 | A | 2/1974 | Schulte |
| 3,815,576 | A | 6/1974 | Balaban |
| 3,858,783 | A | 1/1975 | Kapitanov et al. |
| 3,924,633 | A | 12/1975 | Cook et al. |
| 3,995,619 | A | 12/1976 | Glatzer |
| 4,019,499 | A | 4/1977 | Fitzgerald |
| 4,037,603 | A | 7/1977 | Wendorff |
| 4,128,100 | A | 12/1978 | Wendorff |
| 4,172,458 | A | 10/1979 | Pereyra |
| 4,235,238 | A | 11/1980 | Ogiu et al. |
| 4,246,660 | A | 1/1981 | Wevers |
| 4,441,497 | A | 4/1984 | Paudler |
| 4,509,516 | A | 4/1985 | Richmond |
| 4,548,202 | A | 10/1985 | Duncan |
| 4,585,437 | A * | 4/1986 | Simms ............ 604/106 |
| 4,632,100 | A | 12/1986 | Somers et al. |
| 4,775,380 | A | 10/1988 | Seedhom et al. |
| 4,857,041 | A | 8/1989 | Annis et al. |
| 4,865,031 | A | 9/1989 | O'Keeffe |
| 4,873,976 | A | 10/1989 | Schreiber |
| 4,920,986 | A | 5/1990 | Biswas |
| 4,932,962 | A | 6/1990 | Yoon et al. |
| 4,938,760 | A | 7/1990 | Burton et al. |
| 4,969,892 | A | 11/1990 | Burton et al. |
| 5,007,894 | A | 4/1991 | Enhorning |
| 5,012,822 | A | 5/1991 | Schwarz |
| 5,013,292 | A | 5/1991 | Lemay |
| 5,013,316 | A | 5/1991 | Goble et al. |
| 5,019,032 | A | 5/1991 | Robertson |
| 5,032,508 | A | 7/1991 | Naughton et al. |
| 5,036,867 | A | 8/1991 | Biswas |
| 5,053,043 | A | 10/1991 | Gottesman et al. |
| 5,085,661 | A | 2/1992 | Moss |
| 5,112,344 | A | 5/1992 | Petros |
| 5,123,428 | A | 6/1992 | Schwarz |
| 5,141,520 | A | 8/1992 | Goble et al. |
| 5,149,329 | A | 9/1992 | Richardson |
| 5,188,636 | A | 2/1993 | Fedotov |
| 5,209,756 | A | 5/1993 | Seedhom et al. |
| 5,250,033 | A | 10/1993 | Evans et al. |
| 5,256,133 | A | 10/1993 | Spitz |
| 5,269,783 | A | 12/1993 | Sander |
| 5,281,237 | A | 1/1994 | Gimpelson |
| 5,328,077 | A | 7/1994 | Lou |
| 5,337,736 | A | 8/1994 | Reddy |
| 5,362,294 | A | 11/1994 | Seitzinger |
| 5,368,595 | A | 11/1994 | Lewis |
| 5,370,650 | A | 12/1994 | Tovey et al. |
| 5,370,662 | A | 12/1994 | Stone et al. |
| 5,376,097 | A | 12/1994 | Phillips |
| 5,383,904 | A | 1/1995 | Totakura et al. |
| 5,386,836 | A | 2/1995 | Biswas |
| 5,403,328 | A | 4/1995 | Shallman |
| 5,404,870 | A * | 4/1995 | Brinkerhoff et al. ......... 600/184 |
| 5,413,598 | A | 5/1995 | Moreland |
| 5,439,467 | A | 8/1995 | Benderev et al. |
| 5,474,518 | A | 12/1995 | Velazquez |
| 5,474,543 | A | 12/1995 | McKay |
| 5,518,504 | A | 5/1996 | Polvak |
| 5,520,700 | A | 5/1996 | Beyar et al. |
| 5,520,703 | A | 5/1996 | Essig |
| 5,527,342 | A | 6/1996 | Pietrzak et al. |
| 5,544,664 | A | 8/1996 | Benderev et al. |
| 5,562,689 | A | 10/1996 | Green et al. |
| 5,571,139 | A | 11/1996 | Jenkins, Jr. |
| 5,582,188 | A | 12/1996 | Benderev et al. |
| 5,591,163 | A | 1/1997 | Thompson |
| 5,591,206 | A | 1/1997 | Moufarrege |
| 5,611,515 | A | 3/1997 | Benderev et al. |
| 5,628,756 | A | 5/1997 | Barker, Jr. et al. |
| 5,633,286 | A | 5/1997 | Chen |
| 5,643,320 | A | 7/1997 | Lower et al. |
| 5,669,935 | A | 9/1997 | Rosenman et al. |
| 5,683,349 | A | 11/1997 | Makower et al. |
| 5,697,931 | A | 12/1997 | Thompson |
| 5,709,708 | A | 1/1998 | Thal |
| 5,725,541 | A | 3/1998 | Anspach, III et al. |
| 5,741,282 | A | 4/1998 | Anspach, III et al. |
| 5,782,916 | A | 7/1998 | Pintauro et al. |
| 5,785,640 | A | 7/1998 | Kresch et al. |
| 5,807,403 | A | 9/1998 | Beyar et al. |
| 5,836,314 | A | 11/1998 | Benderev et al. |
| 5,836,315 | A | 11/1998 | Benderev et al. |
| 5,840,011 | A | 11/1998 | Landgrebe et al. |
| 5,842,478 | A | 12/1998 | Benderev et al. |
| 5,860,425 | A | 1/1999 | Benderev et al. |
| 5,899,909 | A | 5/1999 | Claren et al. |
| 5,919,232 | A | 7/1999 | Chaffringeon et al. |
| 5,922,026 | A | 7/1999 | Chin |
| 5,925,047 | A | 7/1999 | Errico et al. |
| 5,934,283 | A | 8/1999 | Willem et al. |
| 5,935,122 | A | 8/1999 | Fourkas et al. |
| 5,944,732 | A | 8/1999 | Raulerson et al. |
| 5,954,057 | A | 9/1999 | Li |
| 5,972,000 | A | 10/1999 | Beyar et al. |
| 5,976,146 | A * | 11/1999 | Ogawa et al. ............ 606/86 R |
| 5,980,558 | A | 11/1999 | Wiley |
| 5,984,927 | A | 11/1999 | Wenstrom, Jr. |
| 5,988,171 | A | 11/1999 | Sohn et al. |
| 5,997,554 | A | 12/1999 | Thompson |
| 6,010,447 | A | 1/2000 | Kardjian |
| 6,027,523 | A | 2/2000 | Schmieding |
| 6,030,393 | A | 2/2000 | Corlew |
| 6,031,148 | A | 2/2000 | Hayes et al. |
| 6,036,701 | A | 3/2000 | Rosenman |
| 6,039,686 | A | 3/2000 | Kovac |
| 6,042,534 | A | 3/2000 | Gellman et al. |
| 6,042,536 | A | 3/2000 | Tihon et al. |
| 6,042,583 | A | 3/2000 | Thompson et al. |
| 6,048,351 | A | 4/2000 | Gordon et al. |
| 6,050,937 | A | 4/2000 | Benderev |
| 6,053,935 | A | 4/2000 | Brenneman et al. |
| 6,056,688 | A | 5/2000 | Benderev et al. |
| 6,068,591 | A | 5/2000 | Bruckner et al. |
| 6,071,290 | A | 6/2000 | Compton |
| 6,074,341 | A | 6/2000 | Anderson et al. |
| 6,077,216 | A | 6/2000 | Benderev et al. |
| 6,099,538 | A | 8/2000 | Moses |
| 6,099,551 | A | 8/2000 | Gabbay |
| 6,099,552 | A | 8/2000 | Adams |
| 6,106,545 | A | 8/2000 | Egan |
| 6,110,101 | A | 8/2000 | Tihon et al. |
| 6,117,067 | A | 9/2000 | Gil-Vernet |
| 6,127,597 | A | 10/2000 | Beyar et al. |
| 6,168,611 | B1 | 1/2001 | Rizvi |
| 6,200,330 | B1 | 3/2001 | Benderev et al. |
| 6,221,005 | B1 | 4/2001 | Bruckner et al. |
| 6,241,736 | B1 | 6/2001 | Sater et al. |
| 6,264,676 | B1 | 7/2001 | Gellman et al. |
| 6,273,852 | B1 | 8/2001 | Lehe et al. |
| 6,302,840 | B1 | 10/2001 | Benderev |
| 6,306,079 | B1 | 10/2001 | Trabucco |
| 6,322,492 | B1 | 11/2001 | Kovac |
| 6,328,686 | B1 | 12/2001 | Kovac |
| 6,328,744 | B1 | 12/2001 | Harari et al. |
| 6,334,446 | B1 | 1/2002 | Beyar |
| 6,352,553 | B1 | 3/2002 | van de Burg et al. |
| 6,364,832 | B1* | 4/2002 | Propp ............ 600/220 |
| 6,382,214 | B1 | 5/2002 | Raz et al. |
| 6,383,191 | B1* | 5/2002 | Zdeblick et al. ............ 606/105 |
| 6,387,041 | B1 | 5/2002 | Harari et al. |
| 6,406,423 | B1 | 6/2002 | Scetbon |
| 6,406,480 | B1 | 6/2002 | Beyar et al. |
| 6,414,179 | B1 | 7/2002 | Banville |
| 6,423,080 | B1 | 7/2002 | Gellman et al. |
| 6,451,024 | B1 | 9/2002 | Thompson et al. |
| 6,475,139 | B1 | 11/2002 | Miller |
| 6,478,727 | B2 | 11/2002 | Scetbon |
| 6,482,214 | B1 | 11/2002 | Sidor, Jr. et al. |
| 6,491,703 | B1 | 12/2002 | Ulmsten |
| 6,494,906 | B1 | 12/2002 | Owens |
| 6,502,578 | B2 | 1/2003 | Raz et al. |

(56) References Cited

U.S. PATENT DOCUMENTS

| | | |
|---|---|---|
| 6,506,190 B1 | 1/2003 | Walshe |
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,179,263 B2 * | 2/2007 | Zdeblick ............ A61B 17/1757 606/90 |
| 7,198,597 B2 | 4/2007 | Siegel et al. |
| 7,226,407 B2 | 6/2007 | Kammerer |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,374,534 B2 * | 5/2008 | Dalton ......................... 600/222 |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Bryon et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosley et al. |
| 7,789,821 B2 | 9/2010 | Browning |
| 7,981,024 B2 | 7/2011 | Levy |
| 8,172,745 B2 | 5/2012 | Rosenblatt |
| 2001/0007073 A1 * | 7/2001 | Zucherman et al. ........... 606/61 |
| 2001/0011170 A1 * | 8/2001 | Davison et al. ............... 604/500 |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0116777 A1 * | 6/2004 | Larson et al. ................. 600/210 |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0106416 A1 * | 5/2006 | Raymond et al. ............. 606/198 |
| 2006/0122457 A1 | 6/2006 | Kovac |
| 2006/0128828 A1 | 7/2006 | Cox et al. |
| 2006/0167487 A1 * | 7/2006 | Hamada ........................ 606/198 |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0073110 A1 * | 3/2007 | Larson et al. ................. 600/210 |

(56) References Cited

U.S. PATENT DOCUMENTS

| | | | |
|---|---|---|---|
| 2007/0078295 A1 | 4/2007 | landgrebe | |
| 2007/0173864 A1 | 7/2007 | Chu | |
| 2007/0219416 A1* | 9/2007 | Perez-Cruet et al. | 600/219 |
| 2008/0039678 A1 | 2/2008 | Montpetit et al. | |
| 2008/0132764 A1* | 6/2008 | Hamada | 600/201 |
| 2008/0140218 A1 | 6/2008 | Staskin et al. | |
| 2008/0300607 A1 | 12/2008 | Meade et al. | |
| 2009/0005634 A1 | 1/2009 | Rane | |
| 2009/0012353 A1 | 1/2009 | Beyer | |
| 2009/0221868 A1 | 9/2009 | Evans | |
| 2010/0022822 A1 | 1/2010 | Walshe | |
| 2010/0179575 A1 | 7/2010 | Von Pechmann et al. | |
| 2010/0261950 A1 | 10/2010 | Lund | |
| 2010/0280627 A1 | 11/2010 | Hanes, II | |
| 2011/0124954 A1 | 5/2011 | Ogdahl et al. | |
| 2011/0174313 A1 | 7/2011 | Von Pechmann et al. | |
| 2011/0301424 A1* | 12/2011 | Steigerwald | 600/235 |
| 2012/0016185 A1 | 1/2012 | Sherts et al. | |
| 2013/0296686 A1* | 11/2013 | Sarna | A61B 1/00147 600/407 |

FOREIGN PATENT DOCUMENTS

| | | |
|---|---|---|
| DE | 2305815 A1 | 8/1974 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A1 | 10/1987 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO1999/059477 | 11/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004/017862 | 3/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

"Access Instrument System with AlloSling Fascia" (5 pages with two pages of Instructions for Use).

"Introducing: AlloSling Fascia The *Natural Choice* for Suburethral Sling Procedures", Advertisement from UroMed Corporation (1 page).

"We're staying ahead of the curve" Introducing the IVS Tunneller Device for Tension Free Procedures, Tyco Healthcare, 3 pages (2002).

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

AlloSource product literature (11pages).

Amundsen, Cindy L. et al., Anatomical Correction of Vaginal Vault Prolapse by Uterosacral Ligament Fixation in Women who also Require a Pubovaginal Sling, The Journal of Urology, vol. 169, pp. 1770-1774, (May 2003).

Araki, Tohru et al., The Loop-Loosening Procedure for Urination Difficulties After Stamey Suspension of the Vesical Neck, The Journal of Urology, vol. 144, pp. 319-323 (Aug. 1990).

(56) References Cited

OTHER PUBLICATIONS

Asmussen, M. et al., Simultaneous Urethro-Cystometry With a New Technique, Scand J Urol Nephrol 10, p. 7-11 (1976).
Beck, Peter R. et al., Treatment of Urinary Stress Incontinence With Anterior Colporrhaphy, Obstetrics and Gynecology, vol. 59, (No. 3), pp. 269-274 (Mar. 1982).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).
Blaivas, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn. vol. 31, pp. 281-290 (1961).
Capio™ CL—Transvaginal Suture Capturing Device—Transvaginal Suture Fixation to Cooper's Ligament for Sling Procedures, Boston Scientific, Microvasive®, 8 pages, (2002).
Cervigni, Mauro et al., The use of Synthetics in the Treatment of Pelvic Organ Prolapse, Voiding Dysfunction and Female Urology, vol. 11, pp. 429-435 (2001).
Choe, Jong M. et al., Gore-Tex Patch Sling: 7 Years Later, Urology, vol. 54, pp. 641-646 (1999).
Comparison of Tissue Reaction of Monofilament and Multifilament Polypropylene Mesh—A Case Report, Tyco Healthcare, United States Surgical, 4 pages (no date).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodiance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.
Decter, Ross M., Use of the Fascial Sling for Neurogenic Incontinence: Lessons Learned, The Journal of Urology, vol. 150, pp. 683-686 (Aug. 1993).
Delancey, John, MD, Structural Support of the Urethra as it Relates to Stress Urinary Incontinence: The Hammock Hypothesis, Am J Obstet Gynecol, vol. 170, No. 6, pp. 1713-1723 (Jun. 1994).
Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh, Tolerance and short-term results of a 103 case continuous series, Gynecologie Obstetrique & Fertilite, vol. 31, Issue 1, pp. 14-19 (Jan. 2003).

Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pp. 45-50 (1990).
Falconer, C. et al., Clinical Outcome and Changes in Connective Tissue Metabolism After Intravaginal Slingplasty in Stress Incontinence Women, International Urogynecology Journal, pp. 133-137 (1966).
Falconer, C. et al., Influence of Different Sling Materials of Connective Tissue Metabolism in Stress Urinary Incontinent Women, International Urogynecology Journal, Supp. 2, pp. S19-S23 (2001).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operation (Transvaginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987).
Guner, et al., Transvaginal Sacrospinous Colpopexy for Marked Uterovaginal and Vault Prolapse, Inter J of Gynec & Obstetrics, vol. 74, pp. 165-170 (2001).
Gynecare TVT Tension-Free Support for Incontinence, The tension-free solution to female Incontinence, Gynecare Worldwide, 6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101, n. 6, pp. 1279-1284 (Jun. 2003).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontience: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetric & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
Intramesh L.I.F.T. Siliconized polyester, Cousin Biotech, 1 page (no date).
Intramesh L.I.F.T.® Polypropylene Less invasive Free tape, Cousin Biotech, 2 pages (no date).
IVS Tunneller—A Universal Instrument for anterior and posterior intra-vaginal tape placement, Tyco Healthcare, 4 pages (Aug. 2002).
IVS Tunneller—ein universeiles Instrument fur die Intra Vaginal Schlingenplastik, Tyco Healthcare, 4 pages (2001).
IVS Tunneller, AMA, (no date) 4 pages.
IVS Tunneller, Australian Medical Desgin Breakthrough for GSI, mixed incontinence and vault prolapse, AMA Medical Products, 4 pages (no date).
Jeffcoate, T.N.A. et al., The Results of the Aldridge Sling Operation for Stress Incontinence, Journal of Obstetrics and Gynaecology, pp. 36-39 (1956).

(56) References Cited

OTHER PUBLICATIONS

Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgety, (Walter & Karram eds.) pp. 235-256 (Mosby 1999).
Kersey, J., The Gauze Hammock Sling Operation in the Treatment of Stress Incontintence, British Journal of Obstetrics and Gynaecology, vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2 pp. 294-296 (Aug. 1996).
Klutke, John M.D. et al, The promise of tension-free vaginal tape for female SUI, Contemporary Urology, 7 pages. (Oct. 2000).
Korea, A. et al., Experience With Silastic Slings for Female Urinary Incontience, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kova, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Leach, Gary E., et al., Female Stress Urinary Incontinence Clinical Guidelines Panel Report on Surgical Management of Female Stress Urinary Incontinence, American Urological Association, vol. 158, 875-880 (Sep. 1997).
Leach, Gary E., MD, Bone Fixation Technique for Transvaginal Needle Suspension, Urology vol. XXXI, No. 5, pp. 388-390 (May 1986).
Lichtenstein, Irving L. et al, The Tension Free Hernioplasty, The American Journal of Surgery. vol. 157 pp. 188-193 (Feb. 1989).
LigiSure Atlas™, Tyco Healthcare, Valleylab®, 2 pages (no date).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'un Trellis Synthetique Dans La Cure Par Voie Vaginale Des Prolapsus Genitaux, J Gynecol Obstet Biol Reprod, vol. 28, pp, 825-829 (1999).
Marchionni, Mauro et el., True Incidence of Vaginal Vault Prolapse—Thirteen Years of Experience, Journal of Reproductive Medicine, vol. 44, n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Marshall, Victor Fray et al, The Correction of Stress Incontinence by Simple Vesicourethral Suspension, Surgery, Gynecology and Obstetrics, vol. 88, pp. 509-518 (1949).
McGuire, Edward J. et al., Pubovaginal Sling Procedure for Stress Incontinence, The Journal of Urology, vol. 119, pp. 82-84 (Jan. 1978).

McGuire., Edward J. et al., Abdominal Procedures for Stress Incontinence, Urologic Clinics of North America, pp. 285-290, vol. 12, No. 2 (May 1985).
McGuire, Edward J. et al., Experience With Pubovaginal Slings for Urinary Incontinence at the University of Michigan, Journal of Urology, vol. 138, pp. 90-93(1987).
McGuire, Edwared J. et al., Abdominal Fascial Slings, Slings, Raz Female Urology, p. 369-375 (1996).
McGuire, Edwared J., M.D., The Sling Procedure for Urinary Stress Incontinence, Profiles in Urology, pp. 3-18.
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr., et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto et al., Treatment Results Using a Mixed Fiber Mesh in Patients With Grade IV Cystocele, Journal of Urology, vol. 161, pp. 1255-1258 (Apr. 1999).
Mitek Brochure, Therapy of Urinary Stress Incontinence in Women Using Mitek Glil Anchors, By Valenzio C. Mascio, MD.
Moir, J. Chassar et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., A Simplified Sling Operation Suitable for Routine Use, Gynecological and Obstetrical Clinic, University of Vienna, vol. 84, No. 3, p. 400-405 (Aug. 1, 1962).
Natale, F. et al., Tension Free Cystocele Repair (TCR): Long-Term Follow-Up, International Urogynecology Journal, vol. 11, supp. 1, p. S51 (Oct. 2000).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al, Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1, pp. 45-50 (1999).

(56) References Cited

OTHER PUBLICATIONS

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69, Sup 153, p. 75 (1990).
Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetricia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa of al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pelvic Floor Rehabilitation According to the Integrated Theory of Female Urinary Incontinence, Chapter 7, pp. 249-258 (book chapter).
Petros, Peter E. Papa et al., Pregnancy Effects on the Intravaginal Sling Operation, Acta Obstet Gynecol Scand, vol. 69 Sup 153, pp. 77-79(1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153 pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153 pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics Sup 153, pp. 77-79 (1993).
Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a Lax Posterior Vaginal Fornix in the Causation of Stress and Urgency Symptoms: A Preliminary Report, Acta Obstet Gynecol Scand, vol. 69, Sup 153, pp. 71-73 (1990).
Petros, Peter E. Papa et al., The Tethered Vagina Syndrome, Post Surgical Incontinence and I-Plasty Operation for Cure, Acta Obstet Gynecol Scand, vol. 69, Sup 153 pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II, Restoration of Dynamic Vaginal Supports by Infracoccygeal Sacropexy, an Axial Day-Case Vaginal Procedure, Int Urogynecol J, vol. 12 pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, p. 46,48,49 (Jun. 2000).
Raz, Shlomo et al., The Raz Bladder Neck Suspension Results in 206 Patients, The Journal of Urology, pp. 845-846 (1992).
Raz, Shlomo, Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Readjustable REMEEX® system, Neomedic International, 8 pages (no date).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).

(56) References Cited

OTHER PUBLICATIONS

Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
Sabre™ Bioabsorbable Sling, Generation Now, Mentor 4 pages (May 2002).
Sabre™ Surgical Procedure, Mentor, 6 pages (Aug. 2002).
Sanz, Luis E. et al., Modification of Abominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin et al., A Comparison Tensile Strength among Three Preparations of Irradiated and Non-Irradiated Human Fascia Lata Allografts (2 pages).
Staskin, David R. et al., The Gore-Tex Sling Procedure for Female Sphincteric Incontinence: Indications, Technique, and Results, World Jornal of Urology, vol. 15, pp. 295-299 (1997).
Studdiford, William E., Transplantation of Abdominal Fascia for the Relief of Urinary Stress Incontinence, American Journal of Obstetrics and Gynecology, pp. 764-775 (1994).
Subak, Leslee L. et al. Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Suport™, Sub-Urethral Perineal Retro-Pubic Tensionless Sling. Matrix Medical (Pty) Ltd, (no date), 1 pg.
Swift, S.E., et al., Case-Control Study of Etiologic Factors in the Development of Sever Pelvic Organ Prolapse, Int Urogynecol J, vol. 12, pp. 187-192 (2001).
T-Sling® (Totally Tension-free) Urinary Incontinence Procedure, Herniamesh, 2 pages (no date).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—a Sympton, not a Urodynamic Disease. Some Theoretical and Practical Aspects on the Diagnosis a Treatment of Female Urinary Incontinence, International Urogynecology Journal, vol 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slinplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1 pp. 93-97 (Sep. 1, 1982).
UroMed Access Instrument System for the Sub-urethral Sling Procedure Catalog No. 120235, Directions for Use, (3 pages).
Vesica® Percutaneous Bladder Neck Stabilization Kit, A New Approach to Bladder Neck Suspenison, Microvasive® Boston Scientic Corporation, 4 pages (1995).
Vesica® Sling Kits, Simplifying Sling Procedures, Microvasive® Bostion Scientific Corporation, 4 pages (1998).
Villet, R., Reponse De R. Villet À L'Article De D. Dargent et al., Gynécolgie Obstétrique & Fertilité, vol. 31, p. 96 (2003).
Visco, Anthony G. et al., Vaginal Mesh Erosion After Abdominal Sacral Colpopexy, Am J Obstet Gynecol, vol. 184, n. 3, pp. 297-302 (297-302).
Walters, Mark D., Percutaneous Subrethral Slings: State of the Art, Presented at the conference of the American Urogynecologic Society, Chicago, 29 pages (Oct. 2001).
Waxman, Steve et al., Advanced Urology Surgery for Urinary Incontinence, The Female Patient, pp. 93-100, vol. 21, (Mar. 1996).
Weber, Anne M. et al., Anterior Vaginal Prolapse. Review of Anatomy and Techniques of Surgical Repair: Obstetrics and Gynecology, vol. 89, n. 2, pp. 311-318 (Feb. 1997).
Webster, George D., Female Urinary Incontinence, Urologic Surgery, pp. 665-679.
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology vol. 135 pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist vol. 2, No. 1, pp. 29-36 (Apr. 1994).
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology and Nephrology Supplement 153: p. 1 (1993).
Horbach, Nicollette, Suburethral Sling Procedures, Genuine Stress Incontinence, Chapter 42, pp. 569-579.
Henriksson, L., et al., "A Urodynamic Evaluation of the Effects of Abdominal Urethrocystopexy and Vaginal Sling Urethroplasty in

(56) References Cited

OTHER PUBLICATIONS

Women With Stress Incontinence", Am. J. Obstet. Gynecol, vol. 131, No. 1, Mar. 1, 1978, pp. 77-82.
Petros, et al., "The Autogenic Ligament Procedure: A Technique for Planned Formation of an Artificial Neo-Ligament", Acta Obstet Gynecol Scand, vol. 69, Sup 153, 1990, pp. 43-51.

* cited by examiner

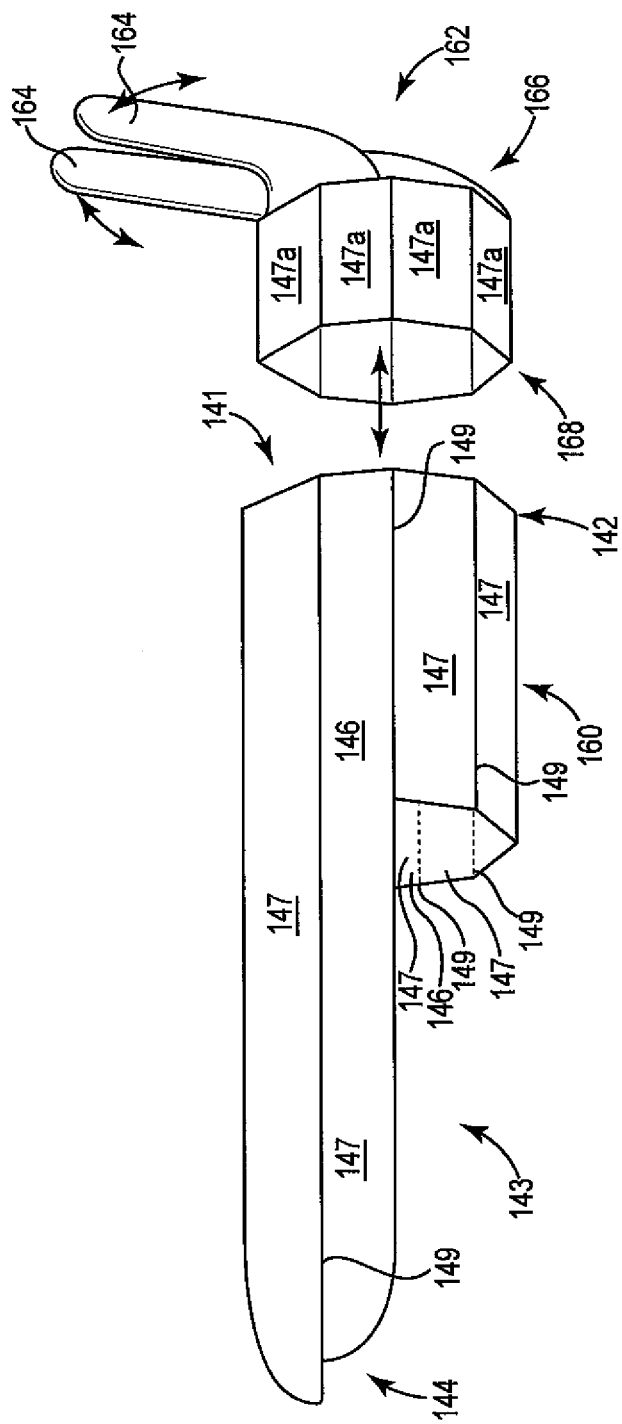
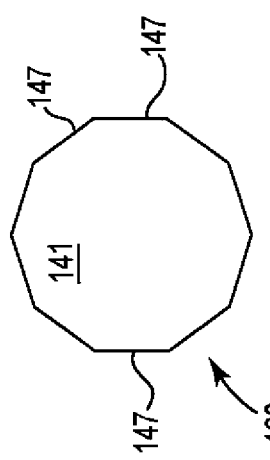
Fig. 3A
Fig. 3B

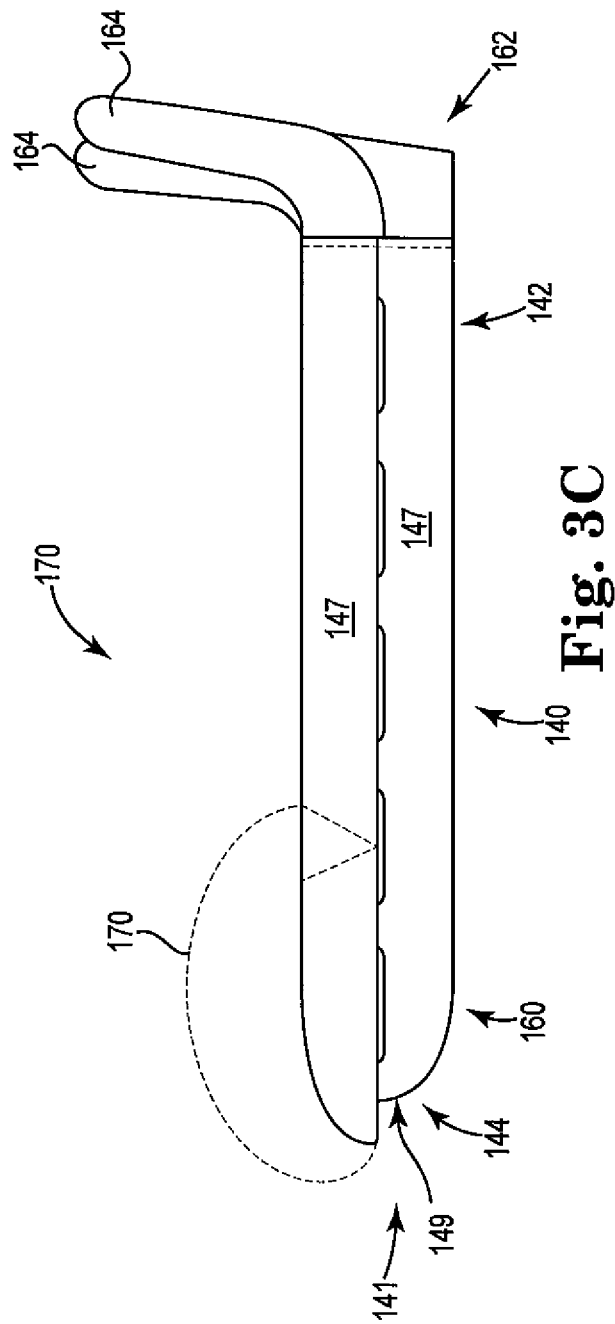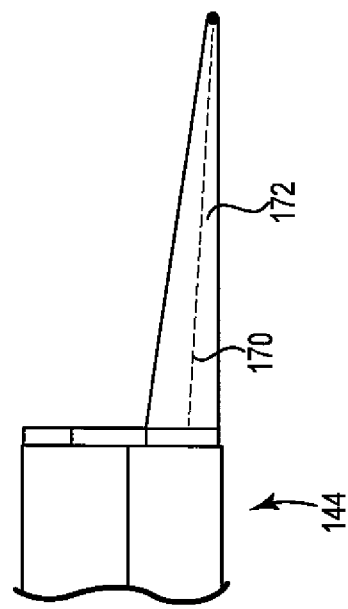

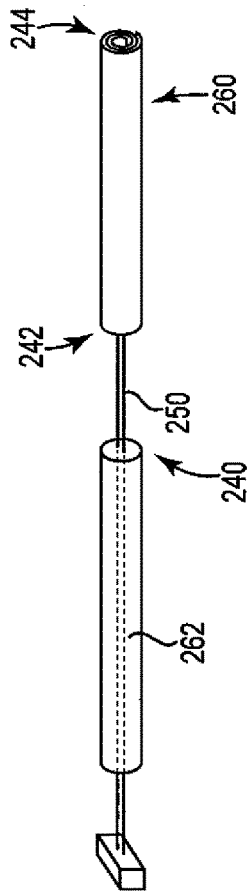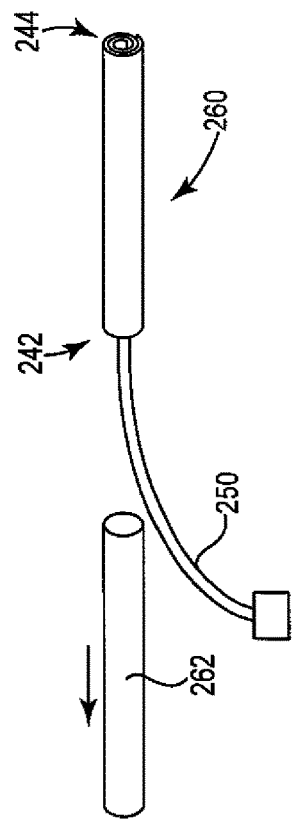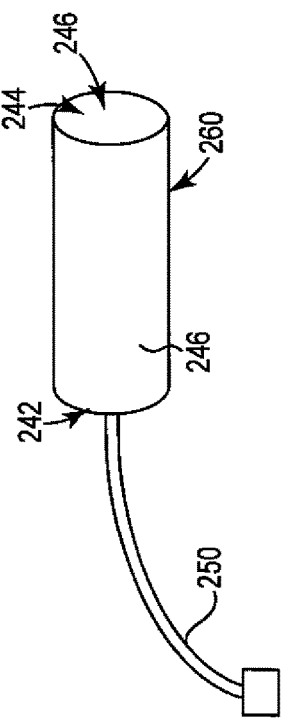

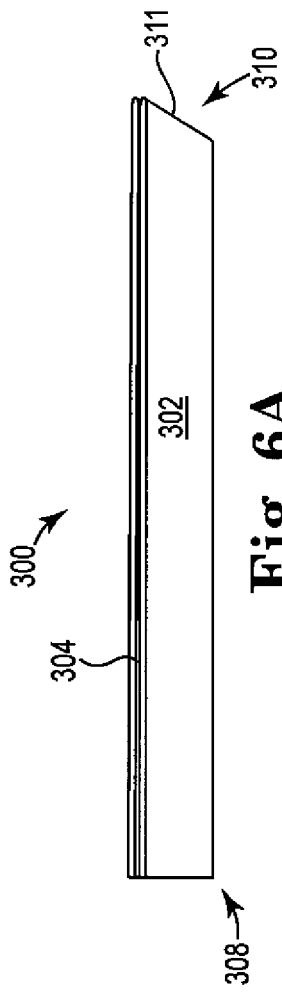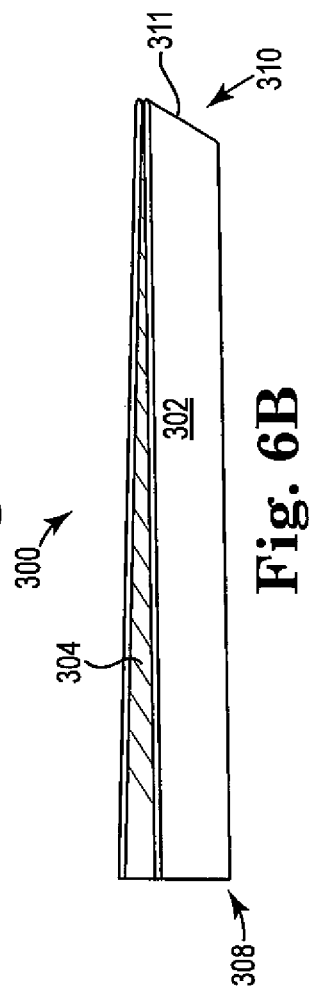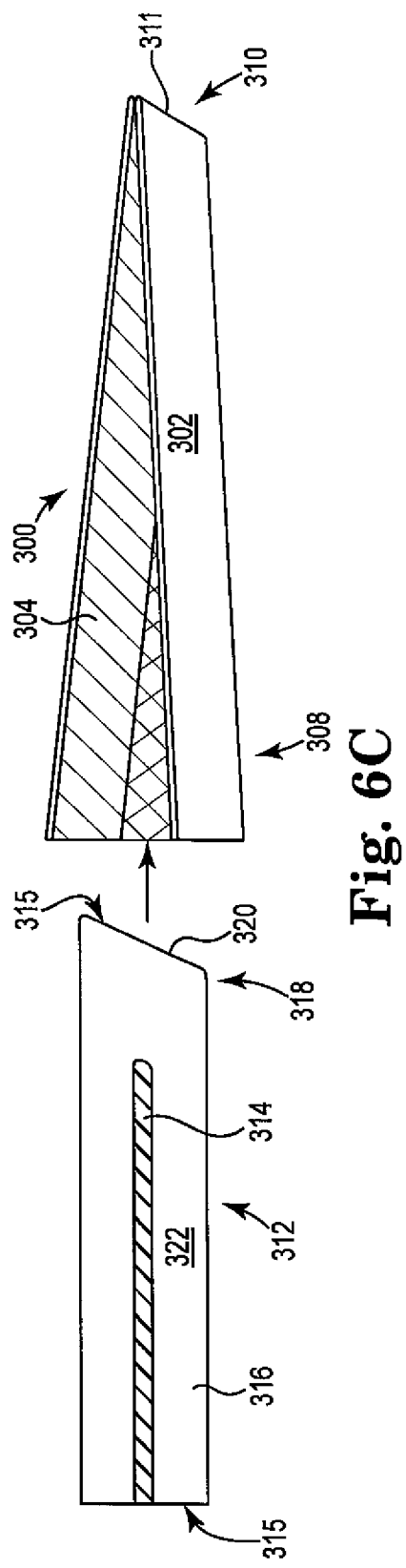

SYSTEMS, IMPLANTS, TOOLS, AND METHODS FOR TREATMENTS OF PELVIC CONDITIONS

PRIORITY CLAIM

The present non-provisional patent application claims priority under 35 USC § 119(e) from United States Provisional Patent Application having Ser. No. 61/502,694, filed Jun. 29, 2011, entitled "SYSTEMS, IMPLANTS, TOOLS, AND METHODS FOR TREATMENTS OF PELVIC CONDITIONS," the entirety of which is incorporated herein by reference.

FIELD OF THE INVENTION

The invention relates generally to systems, tools, and related methods for treating pelvic conditions including but not limited to prolapse conditions, for example treatment of vaginal and vaginal vault prolapse by transvaginal, abdominal, and laparoscopic procedures, such as by a transvaginal, abdominal, or laparoscopic sacral colpopexy procedure.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Abdominal sacralcolpopexy (SCP) is considered to be an especially efficacious treatment, but it can be complicated and is generally considered invasive.

There is ongoing desire and need for minimally invasive yet highly effective methods of implanting supportive implants for treating pelvic conditions in male and female patients, such as vaginal prolapse and other pelvic conditions.

SUMMARY

Devices, systems, and methods as described can be used in the treatment of pelvic conditions such as vaginal prolapse (including various forms such as enterocele, cystocele, rectocele, apical or vault prolapse, uterine descent, etc.), and other conditions caused by muscle and ligament weakness, hysterectomies, and the like, in a male and female patients.

Various surgical tools, structures, implants, expansion members ("retractors"), and procedural improvements are described herein for use in treating pelvic conditions. These items can be used in procedures for placing a pelvic implant in a therapeutic location in a male or a female patient, by a method of accessing pelvic tissue, the method involving a vaginal incision or an abdominal incision such as a laparoscopic incision.

Certain described embodiments relate generally to surgical methods and apparatus and, more specifically, to surgical tools having surfaces capable of retracting tissue (a retractor, such as an expansion member), and adapted to provide access and guidance to a surgical site. These embodiments involve various surgical tools and related methods designed to provide improved and safer access to a surgical site or anatomy, for example so that sharp objects and tools can be passed to a surgical location without having to make multiple attempts from an incision to an anatomical target area. Certain of these described embodiments relate generally to various means, devices, and techniques for providing a clear view and unobstructed access to a sacrum, through a vaginal incision or an abdominal incision (e.g., laparoscopically). In several examples, desired utility of a retractor and methods can be provided by way of an expandable device, or other devices capable of being used to retract tissue, that can be inserted into a vaginal, laparoscopic, or abdominal incision and then expanded, dilated, or otherwise used for retraction. Certain preferred versions of these tools can include distal end functionality to add efficiency to a surgical procedure, e.g., for performing a transvaginal transabdominal, or laparoscopic sacral colpopexy.

In one aspect, the invention relates to an expansion member that includes a proximal end, a distal end, and a length from the proximal end to the distal end. The distal end can be placed through a surgical incision to provide access to a region of sacral anatomy. The distal end comprises functionality selected from: viewing functionality, lighting functionality, size adjustability, suction, dissection, anchor delivery, implant delivery, fluid delivery, absorption functionality, cauterization functionality, an expandable surface, a suture needle holder, a dissolvable coating at the distal end, and combinations thereof.

In another aspect the invention relates to an expansion member that includes an expansion member piece and a handle piece. The expansion member piece includes a proximal end, a distal end, and a length from the proximal end to the distal end. The distal end can be placed through a surgical incision to provide access to a region of sacral anatomy. The piece is removably engagable with the proximal end.

In another aspect the invention relates to a expansion member that includes an expansion member piece and an introducer piece. The expansion member piece includes a proximal end, a distal end, and a length from the proximal end to the distal end. The distal end can be placed through a surgical incision to provide access to a region of sacral anatomy.

In yet another aspect the invention relates to a method of performing pelvic surgery to support a vaginal apex. The method includes: providing an expansion member as described; inserting the distal end through a surgical incision selected from a vaginal incision and an abdominal incision, and using the expansion member to provide access to a region of sacral anatomy.

In another aspect the invention relates to a method of performing pelvic surgery to support a vaginal apex. The method includes: providing an expansion member comprising an expansion member piece and a handle piece. The expansion member piece includes a proximal end, a distal end, and a length from the proximal end to the distal end. The distal end can be placed through a surgical incision to provide access to a region of sacral anatomy. The handle piece is removably engagable with the proximal end. The method includes inserting the distal end through a surgical incision selected from a vaginal incision and an abdominal incision; using the expansion member to provide access to a region of sacral anatomy; and removing the handle piece from the expansion member piece.

In another aspect the invention relates to a method of performing pelvic surgery to support a vaginal apex. The method comprising includes providing an expansion member comprising an expansion member piece and an introducer piece. The expansion member piece includes a proximal end, a distal end, and a length from the proximal end to the distal end. The distal end can be placed through a surgical incision to provide access to a region of sacral anatomy. The method includes inserting the introducer piece through a surgical incision selected from a vaginal incision and an abdominal incision; inserting the distal end of the expansion member piece into the introducer piece placed in the surgical incision; removing the introducer piece from the incision, and using the expansion member to provide access to a region of sacral anatomy.

In yet another aspect the invention relates to a blunt dissection device that includes a proximal end, a distal end, a shaft extending along a length between the proximal end to the distal end, a handle at the proximal end. A paddle at the distal end includes a surface capable of moving tissue laterally, and a blunt distal edge. The device includes a light at the distal end.

In another aspect the invention relates to a method of performing pelvic surgery to support a vaginal apex. The method includes: providing a blunt dissection device as described herein, inserting the blunt dissection device through a surgical incision selected from a vaginal incision and an abdominal incision, and using the blunt dissection device to retract tissue to provide access to a region of sacral anatomy.

BRIEF DESCRIPTION OF THE DRAWINGS

FIGS. 3A and 3B are side and end views of an expansion member.

FIG. 3C is a side view of an expansion member.

FIG. 4 is a side view of distal end features of an expansion member.

FIGS. 5A, 5B, 5C, and 5D are side views of an expansion member piece and an introducer piece.

FIGS. 6A and 6B are side views of an introducer piece.

FIG. 6C is a side view of an expansion member piece and an introducer piece.

Figures 1A, 1B:
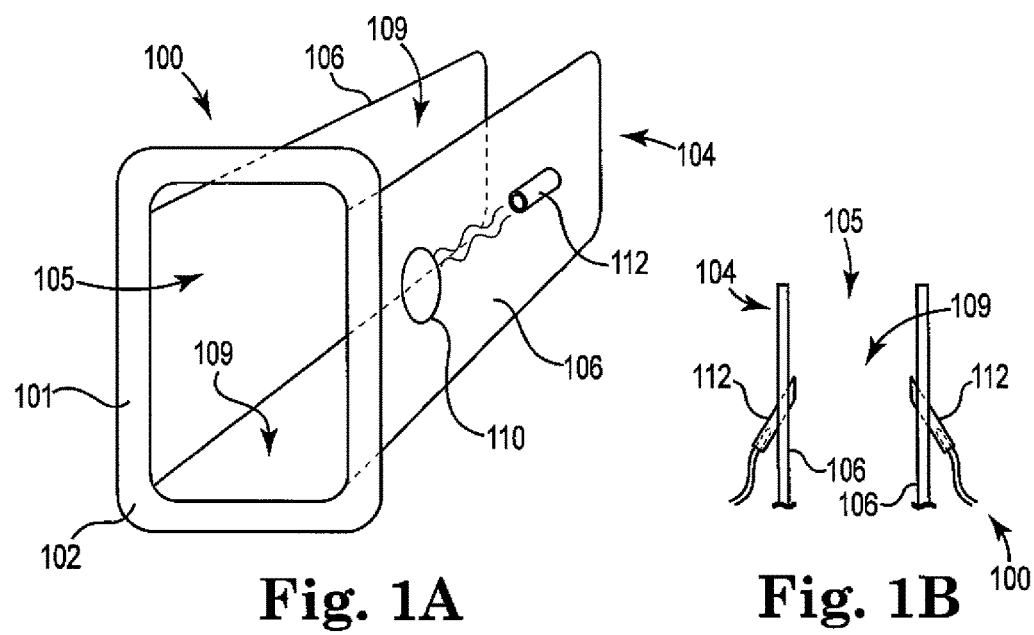
FIGS. 1A, 1B, 1C, and 1D are end perspective, top, side perspective, and end views of an expansion member.
Figure 1C:
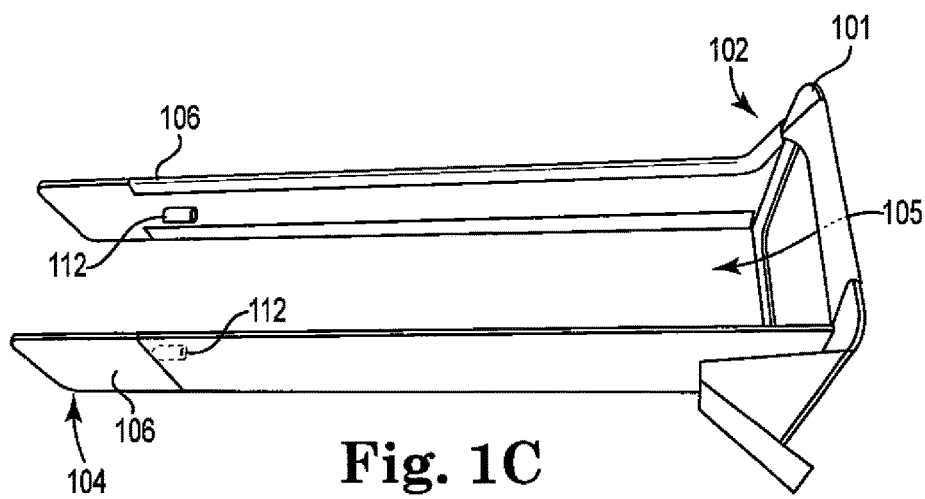
Figure 1D:
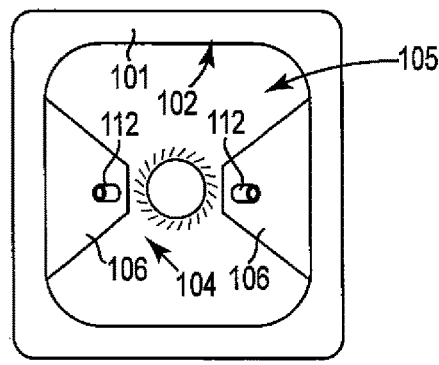

All figures are not to scale.

DETAILED DESCRIPTION

Pelvic floor disorders include cystocele, rectocele, enterocele, incontinence (e.g., urinary and fecal incontinence), and uterine and vaginal vault prolapse, among others. These disorders typically result from weakness or damage to normal pelvic support systems. The most common etiologies include childbearing, removal of the uterus, connective tissue defects, prolonged heavy physical labor and post-menopausal atrophy.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

A sacral colpopexy is a procedure for providing vaginal vault suspension. It may be performed through an abdominal incision, a vaginal incision, or laparoscopically, and entails suspension (by use of an implant such as a strip of mesh) of the vaginal cuff to a region of sacral anatomy such as the sacrum (bone itself), a nearby sacrospinous ligament, uterosacral ligament, or anterior longitudinal ligament at the sacral promontory. In some SCP procedures that also involve a hysterectomy, an implant can attach to posterior vaginal tissue remaining after removal of the uterus and cervix, and attaches also to anatomy to support the vaginal tissue, at or around the sacrum such as to uterosacral ligaments or to the sacrum itself (i.e., to a component of the sacral anatomy).

As used herein, the term "anchor" refers non-specifically to any structure that can connect an implant to tissue of a pelvic region, to secure the implant to that tissue. The tissue may be bone or a soft tissue such as a muscle, fascia, ligament, tendon, or the like. The anchor may be any known or future-developed structure, or a structure described herein, useful to connect an implant to such tissue, including but not limited to a clamp, a suture, a soft tissue anchor such as a self-fixating tip, a helical anchor such as a screw-type or corkscrew-type anchor that can be driven into bone or soft tissue using rotation, a bone anchor (e.g., screw), or other structures known or later developed for connecting an implant to soft tissue or bone of a pelvic region.

Pelvic implant installation procedures (e.g., SCP procedures) may be performed through an abdominal opening, laparoscopically (through a laparoscopic incision in an abdomen), or transvaginally. According to methods described herein, a tissue expander, expansion member, or other retractor device (these terms being used herein interchangeably) can be used to improve access to a surgical site of a pelvic implant installation procedure. A retractor device can be used in the present methods in a minimally invasive transvaginal SCP procedure, or in an abdominal SCP procedure. Examples of methods, tools, expansion members, and soft tissue anchors useful in pelvic procedures are described in Assignee's copending International Patent Application number PCT/US2010/062577, filed Dec. 30, 2010, the entirety of which is incorporated by reference.

As described herein, a retractor or expansion member includes a distal end and a proximal end, the distal end may include distal end functionality such as a lighting functionality, size adjustability, suction, dissection, anchor delivery, implant delivery, fluid delivery, absorption functionality, cauterization functionality, an expandable surface, a suture needle holder, a dissolvable coating at the distal end, among others. By use of a retractor or expansion member having viewing and lighting functions, clear visualization of internal tissue is provided for placement and anchoring of an implant or implant component (e.g., anchor), e.g., to a region of sacral anatomy. A physician is able to guide a distal end or shaft of an implant delivery tool (i.e., "needle") with direct viewing, visually identify potential areas of risk, and guide or steer the end of the delivery tool to a desired target tissue site for placing an anchor, implant, or implant component. With a visualization feature, a faster learning curve is provided for physicians to safely pass the needle with the aid of a scope and optical viewing, and the knowledge from scope usage in surgery is applied to and benefits surgical procedures.

According to presently described systems, devices, and methods, an expansion member (a.k.a., "retractor," "speculum," or the like) can be useful for accessing a male or female pelvic anatomy during a transvaginal (in female patients) or trans-abdominal pelvic procedure, especially a female pelvic anatomy, transvaginally, to access tissue of the posterior pelvic region such as to perform an SCP procedure. An expansion member can have a length to allow such access when placed transabdominally or transvaginally, e.g., a length to allow a distal end of the expansion member to provide access to pelvic tissue, e.g., posterior pelvic tissue, while a proximal end of the tool extends through an abdominal or vaginal incision and to a location external to the patient. The proximal end of the expansion member remains external to the patient during use to allow a surgeon or other user to access and manipulate the proximal end and access a surgical site at the distal end through an inner opening or channel in the expansion member that extends between the proximal end and the distal end. The expansion member includes body wall or sidewall portions that extend lengthwise between the distal end and the proximal end, and may optionally form a full or partial enclosure or tube along some or all of a length between the proximal end and the distal end. Exemplary lengths of an expansion member (or an expansion member piece, or an introducer piece) between a proximal end and a distal end, may be in the range from 13 to 18 centimeters, especially for use in a female patient to transabdominally or transvaginally access a posterior location of a pelvic region such as a region of sacral anatomy.

According to certain embodiments a retractor or expansion member can include body wall portions (e.g., sidewalls) that make up a full or partial enclosure or "tube" (whether a partial tube or complete tube). The body wall portions provide partial or continuous structure and support along a length of the expansion member between the distal end and proximal end, to separate tissue from an inner opening or channel defined at the interior of the body wall portions (e.g., sidewalls). The body wall structure may extend lengthwise along a partial or complete length of the device, and at lateral locations (around a circumference relative to a length-wise axis) the body wall structure can be a complete or partial structure; the body wall structure may form a tube (e.g., circular, rectangular, or of any other desired cross-section) having structure extending around a complete circumference, e.g., a circular or non-circular "tube"; or a body wall structure may extend partially around a circumference, such as in the form of a partial circular or non-circular "tube." The cross-section when viewed along a longitudinal axis may be round or angular, circular, partially-circular, square, rectangular, etc., and may be continuous over the cross-sectional shape or interrupted by on or more openings (longitudinal openings) in the body walls. A cross-sectional diameter or other dimension of such a structure can be useful to allow the device to be inserted and placed with reduced trauma through a vaginal or an abdominal incision. Optionally, as described elsewhere herein, a cross-sectional dimension (e.g., diameter) of the tube can be variable, such as by being expandable (then retractable) after placement of the expansion member within a patient incision, to allow increased and expanded access to tissue at a surgical site.

Preferred expansion members can include one or more functional features at a distal end that allow the tool to be useful to carry out functions such as dissection (a mechanical dissection using a sharp blade, a blunt dissection device using an expandable structure such as a balloon, or hydro-dissection), blunt dissection, viewing (visualization) of a surgical location, illumination of a surgical location, fluid delivery at a surgical location, irrigation at a surgical location, suction at a surgical location, expandability, and placing anchors (bone anchors, soft tissue anchors such as a self-fixating tip, sutures, etc.) into a desired target tissue at a surgical location.

Various embodiments of expansion members are described hereinbelow, and may have general structural and operational features that allow one or more flexible, rigid, or semi-rigid, distal retracting structure to be introduced through an incision (e.g., a vaginal or abdominal incision), to retract internal tissue. In certain (but not all) embodiments the expansion member can be introduced through an incision in a closed, compressed, or reduced-size or reduced-diameter state, then be moved, assembled, or expanded to enlarge a cross-sectional size or related space or inner opening defined by the expansion member structure, such as sidewalls, to push tissue aside to create space in and access to a pelvic region with access to desired anatomy. A preferred size of an expansion member can include a cross sectional dimension (e.g., a width or diameter associated with an inner opening along a length of the device) in the range from 1 to 5 centimeters, such as from 2 to 4 centimeters (these are referred to herein as diameter ranges $d_1$), when an expansion member is in a reduced-size (e.g., closed) configuration. Upon opening, un-compressing, expanding, or assembling, etc., the expansion member, a preferred dimension (e.g., a width or diameter associated with an inner opening or cross section along a length of the expansion member) can be in the range from 2 to 10 centimeters, such as from 3 to 7 centimeters (these are referred to herein as diameter ranges $d_2$). Also generally, an expansion member (or expansion member piece) can include a length dimension (from a proximal to a distal end) that can be selected to work with a particular anatomy (male or female) and procedure (anterior repair, posterior repair, etc.). A length of an expansion member (or expansion member piece) useful in a transvaginal or abdominal method of treating a posterior pelvic condition (e.g., a SCP procedure) can be sufficient to allow the distal end to reach a region of sacral anatomy as a proximal end remains at or outside of a vaginal introitus or an abdominal incision. A related dimension is the "working depth" of such a device, which is the distance between the distal end of the expansion member and the vaginal introitus or abdominal incision when the expansion member is installed, and which can be any dimension useful or desired, e.g., from 13 to 18 centimeters. A distance by which a portion of an expansion member extends proximally, away from a patient, out of the vaginal introitus or abdominal incision, is preferably minimized. Still referring to the use of these devices in transvaginal or abdominal methods of treatment, another relevant dimension is a "working space" dimension, which is a lateral dimension of an inner opening at a proximal end of the device, such as a diameter, which may preferably be in a range from 3 to 8 centimeters; in a transvaginal or abdominal method, this is an approximate diameter of a vaginal introitus or abdominal incision held open by a proximal end of the expansion member.

Various embodiments of devices ("expansion members," "retractors," or "speculums") are contemplated for use in providing access to internal tissue of a pelvic region through an incision in a male or female patient, e.g., as a tissue retractor used to gain access (e.g., transvaginal or transabdominal access) to a posterior region of a female pelvic anatomy. Any of these may be useful according to methods for placing an implant to support pelvic tissue, for example a SCP procedure, using any desired or useful implant, insertions tool, multi-functional tool, anchor, etc.

According to certain embodiments, an expansion member can be designed to have a reduced cross-sectional size and profile in a closed or compressed state for easy entry into a patient (e.g., vaginally or abdominally), and the expansion member can be opened or expanded to open and retract the surrounding tissue between the surgical incision and the surgical area (e.g., posterior pelvic region or a region of sacral anatomy) for improved viewing of the surgical area to keep tissue from interfering with the procedure.

In certain embodiments, an expansion member can be constructed of multiple (e.g., two, three, four, or more) longitudinal panels, sections, or segments, each having a retraction surface, and each connected by a along a longitudinal-extending side or edge, such as by a hinge or other connection. The hinged (or otherwise connected) edge can be curved or straight. The connection (e.g., hinge) can be any form of connection or hinge that creates a moveable connection along the edges of retraction surfaces. A hinge may be a "piano"-style hinge, a flexible adhesive, a flexible polymeric connective material or membrane, a moveable mechanical connection, a flexible adhesive weld, etc.

Figures included herewith show various exemplary embodiments of expansion members and other tools, including certain specific features. FIGS. 1A, 1B, 1C, 1D, 2A, 2B, and 2C show examples of expansion members that include a light at a distal end for illuminating a surgical area (e.g., surgical site) at a pelvic region, when the expansion member is placed within a patient. Referring to FIG. 1A (end perspective view), 1B (top view), 1C (side perspective view), and 1D (end view), expansion member 100 includes proximal end 102, frame 101 at proximal end 102, distal end 104, blades (or sidewalls) 106 extending from proximal end 102 to distal end 104, and inner opening 105. Upper and lower longitudinal openings 109 extend between top and bottom edges of blades 106. A battery (e.g., a 3 volt "coin" battery) 110 is located at a proximal portion of one of blades 106, and connects to a light 112 (light emitting diode, or otherwise) at a location on or toward distal end 104. Light 112 can be any desired light source, such as a light emitting diode (LED). A specific example can be an "ultrabright" 3 millimeter LED, powered by a lithium ion 3 volt battery (e.g., a 20 mm coin type battery). Expansion member 100 and components thereof (e.g., blades 106 and frame 101) can be made of any material, such as stainless steel, Lexan HPS7 polycarbonate, or other polymeric or metal materials. Each blade 106 may be flat or curved (e.g., to form a structure that defines a complete or partial tube (see FIG. 2A)). As one advantage, the use of a light source at a distal end of an expansion member can simplify a surgical procedure by allowing a surgeon to see a targeted tissue without holding a separate light and without moving his or her head to see tissue using a headlamp.

Figure 2A:
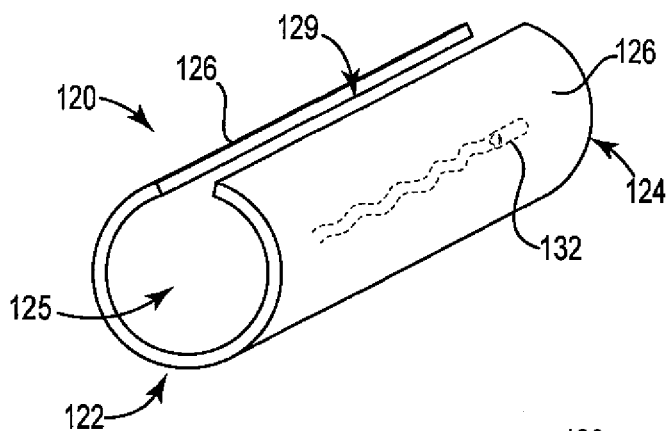
FIGS. 2A, 2B, and 2C are end perspective, end, and end perspective views of an expansion member.
Figure 2B:
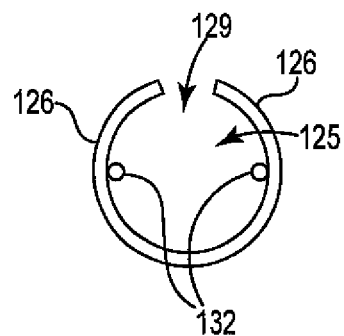
Figure 2C:
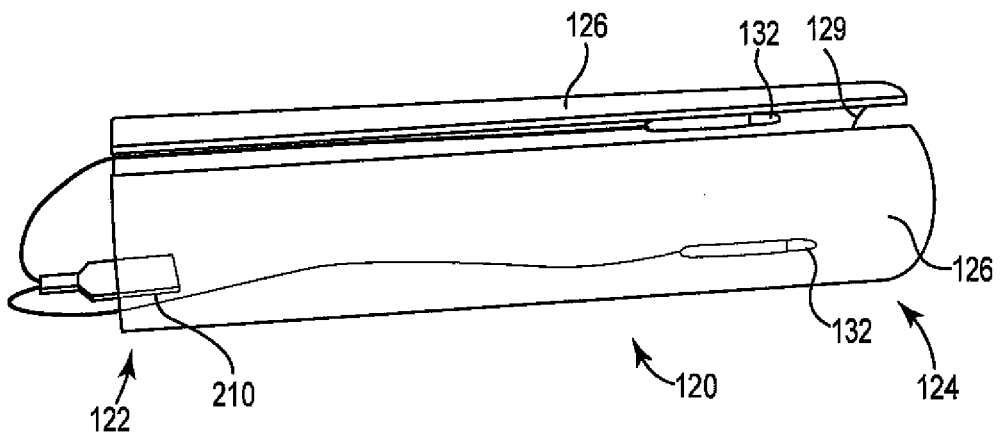

Referring to FIGS. 2A (end perspective view), 2B (end view), and 2C (side perspective view), expansion member 120 includes proximal end 122, distal end 124, sidewalls 126 extending from proximal end 122 to distal end 124, and inner opening 125. Longitudinal opening 129 extends between of opposing sidewalls 126, along a bottom or a top of the length of the device. A battery (e.g., a 3 volt "coin" battery) 210 is located at a proximal portion of one of the sidewalls 126 and connects to lights 132 (light emitting diode, or otherwise) at a location on or toward distal end 124. Lights 132 can be any desired light source, such as a light emitting diode (LED). Expansion member 120 (e.g., sidewalls 126) can be made of any material, such as stainless steel, Lexan HPS7 polycarbonate, or other polymeric or metal materials, and may be flat, cornered, or curved (e.g., to form a structure that defines a complete or partial tube (see FIG. 2A)). As illustrated, expansion member 120 is in the form of a tube having a fixed cross section and length, but other embodiments are also possible, as described.

Various additional or alternate optional features of expansion members may be incorporated, alone or together, with any of the features described elsewhere herein, for use with a method or a device as described. One feature is adjustability of one or more dimension (length, width (e.g., diameter), height) of an expansion member. An expansion member has a cross-sectional width that defines an inner opening, channel, or tube (complete or partial) used to create access to and working space within a pelvic location, such as access to a posterior pelvic location near a sacrum and sacral promontory. The width can be uniform along a length of an expansion member; non-uniform along the length (e.g., wider at a proximal end and narrower at a distal end); or variable at any location along a length, for adjustment before, during, or after a surgical procedure; e.g., a cross-sectional width of an inner opening at a proximal end, at one or more location along a length between a proximal and a distal end, or at a distal end, may be adjustable, each independently of one another, before, during, or after insertion for use during a surgical procedure. A length is a distance between a distal end and a proximal end and may be fixed or may be variable either before, during, or after a surgical procedure (e.g., a length may be adjustable before, during, or after insertion into a patient for use during a surgical procedure). A height is a dimension in the same cross-sectional plane as a width, and can also be fixed or variable at any one or more location along a length of an expansion member, either before, during, or after a surgical procedure.

Optionally an expansion member may not fully enclose a working space along the length or around a circumference of the device between the distal and proximal ends, but may leave one or more portion or side (along the partial or total length of the expansion member) open, giving access to tissue. For example, a "bottom" side of an expansion member may lack structure, leaving an opening along a length of the device (e.g., at the bottom or top; see FIGS. 1A and 2A), to allow access to a peritoneum and fixation of mesh, and anchor, or other implant material, at locations of exposed tissue, e.g., by suturing or use of an anchor. Other features can include a taper (e.g., a narrowing of the shape from the proximal end to the distal end 2; ribs for retention of an expansion member within the patient; sacral mating geometry (shaping of the distal end to match a shape or angle of a sacrum) or materials (e.g., conforming materials such as "tissue wipers") at the far end or tips of one or more segments of a tool; a longitudinal (parallel or approximately parallel to a longitudinal axis or longitudinal dimension of the expansion member) (straight or curved) hinge between moveable segments; selective expansion (adjustment of a width dimension) of an expansion member at different locations along a length of an expansion member, e.g., to match the anatomy of a patient; selective adjustment of a length dimension of an expansion member, e.g., to match the anatomy of a patient; a handle at a proximal end, which may be removable; a lock or ratchet mechanism to maintain one or more selectively set dimensions of an expansion member, or others.

According to exemplary uses of certain described expansion members, including any optional features alone or in combination, a transvaginal vaginal process to reach a sacral promontory can include:

1—Complete an incision through the vaginal apex (or posterior to the apex) and the peritoneum;
2—Place the retractor introducer through the small bowel (optional step);
3—Confirm sacral promontory (bone=firm feel, promontory=increased depth with minimal anterior movement);
4—If the introducer was used, place the retractor (expansion member) over the introducer and push until the tip of the distal end meets the sacrum;
5—Open the retractor
6—Connect a light source (if an external source is used).
7—A working space to the sacrum has been opened and is (optionally) lighted.

When the procedure is performed using an abdominal incision (trans-abdominally) instead of a vaginal incision (transvaginally), the steps can be similar, except that step 1 above is to complete an incision through an abdomen and not a vagina. Optionally, during a procedure, a rectal probe 580 (see FIG. 8J) can be inserted into a rectum of the patient and illuminated to improve viewing of the posterior pelvic region, especially the rectum, colon, and adjacent tissue, to allow avoidance of or manipulation of those tissues during the procedure.

FIG. 4 illustrates an expansion member that may have any one or more features as described, and that includes a delivery tool that can be engaged and disengaged to the retractor at a proximal end. The delivery tool can be used to engage the retractor at a proximal end, manipulate the retractor to place the retractor into a patient, and adjust the retractor such as by increasing a diameter (expanding a cross-sectional dimension and inner opening of the retractor). After the delivery tool is used to place and adjust the size of the retractor, the delivery tool can be disengaged and removed from the proximal end of the retractor. Removing the delivery tool allows improved access to the inner opening and workspace created by the expanded retractor. Advantageously, removing the removable delivery tool from the proximal end will reduce the size and profile of the retractor (proximal end) by removing the handles and delivery mechanism, once the retractor is deployed, giving improved access to the retractor portion placed in the patient.

Referring to FIGS. 3A (side view) and 3B (end view), expansion member 140 includes expansion member piece 160 and detachable handle piece 162. Expansion member piece 160 includes proximal end 142, distal end 144, and sidewalls 146 extending from proximal end 142 to distal end 144. Sidewalls 146 are made of multiple panels 147 held together by longitudinal hinges 149, which, as described herein, may be of various types of hinge construction such as a "piano"-style hinge, an adhesive, a flexible polymeric connective material (e.g., membrane or a "living hinge"), a moveable mechanical connection, a flexible adhesive weld, etc. Inner opening 141 extends lengthwise between proximal end 142 and distal end 144. Bottom opening 143 extends at a bottom of expansion member piece 160, from a location about mid-way along the length of expansion member piece 160, to the distal end of expansion member piece 160. The absence of structure at the bottom of the distal end allows access to tissue of a sacrum, perineum, vaginal tissue, or the like, that will become located at that portion of the expansion member piece 160 when it is installed in a patient.

As illustrated, expansion member piece 160 is in the form of a partial, expandable and retractable tube having a variable cross-sectional dimensions.

FIG. 3B (end view) shows an unfolded or opened cross section with panels 147 being unfolded and arranged to form a cross-sectional, circular, inner opening 141. In a closed configuration (not shown), panels 147 are folded against each other to form a folded or closed configuration of smaller cross sectional dimensions, and a to smaller or absent inner opening 141 between panels. The cross-sectional dimensions of inner opening 141 of expansion member piece 140 can be increased and decreased, i.e., panels 147 can be transitioned between the folded (closed) and unfolded (opened) configurations, by movement of panels 147 about longitudinal hinges 149, by use of handle piece 162.

Handle piece 162 includes handles 164 and body 166. Body 166 includes distal end 168 having engagement surfaces that are capable of releasably engaging proximal end 142 of expansion member piece 160. Engagement surfaces may be any useful surface capable of moving panels 147 between a folded and an unfolded configuration. As illustrated, engagement surfaces are in the form of distal ends of panels 147a, but other forms of engagement surfaces will also be useful. When engagement surfaces of distal end 168 are engaged with proximal end 142, e.g., by individually engaging one or multiple panels 147, handle piece 162 can be used to manipulate expansion member piece 160; for example, handle piece 162 engaged with expansion member piece 160 can be used to insert a folded expansion member piece 160 into a patient incision (e.g., vaginal, abdominal, etc.) and place distal end 144 at a region of sacral anatomy or other desired surgical or pelvic location. Upon such placement within a patient, handles 164 can be manipulated to cause expansion member piece 160 to become unfolded, retracting tissue at the patient incision and at the surgical or pelvic location such as at a region of a sacrum. Next, handle piece 162 can be disengaged from proximal end 142 of expansion member piece 160, providing improved access to inner opening 141 at proximal end 142, for use by a surgeon of installed expansion member piece 160 during a surgical procedure. After performing the surgical procedure, handle piece 162 can be re-engaged with proximal end 142, handle piece 162 can be used to re-configure expansion member piece 160 in a folded configuration, and the assembly of handle piece 162 and expansion portion piece 160 can be removed from the patient.

Other optional details of expansion piece 160 can be as desired and as described herein. Optionally, hinges 149 may be straight or curved and may be capable of ratcheting or locking to allow expansion piece 160 to be locked into an opened (unfolded) or partially opened configuration during a surgical procedure. A ratchet or lock may be releasable by a release mechanism on expansion portion piece 160 or handle piece 162. Panels 147 may be rounded or flat and may be constructed of plastic (e.g., transparent or clear polyacrylate) or metal (e.g., stainless steel). Distal end 144 may include any of the optional features described herein such as a light, irrigation feature, suction, anchor placement feature, dissolvable coating, or the like. A length dimension may be fixed or variable.

FIG. 3C shows an alternate embodiment of an expansion member 140 that includes expansion member piece 160 and handle piece 162. As illustrated, distal end 144 include an optional, expandable tissue approximating structure 170. Tissue approximating structure of a expandable balloon 170 can be any expandable structure at a distal end that can be expanded (e.g., inflated) to retract tissue situated adjacent to tissue approximating structure 170 at distal end 144. Other than an expanding polymeric balloon, tissue approximating structure may be in the form of an expandable metal cage, moveable paddles or other moveable surfaces, or any other moveable structure capable of approximating tissue adjacent to distal end 144. In use, upon placement of distal end 144 at a surgical location such as at a region of sacral anatomy, tissue approximating structure 170 can be actuated and expanded to move tissue away from distal end 144. The expandable structure may be, e.g., an inflatable balloon, and can include a "gauzy" surface that is capable of retracting (pushing away) tissue, e.g., viscera, from a surgical site at the distal end of the device when installed through a surgical incision (transvaginally or trans-abdominally) in a patient to access a posterior pelvic location such as a sacrum.

FIG. 4 illustrates an embodiment of a distal end of a retractor (expansion member) that includes an elongate, needle-like extension or tip. The tip can engage tissue and can be coated with a dissolvable or bioabsorbable material that will dissolve in a short time (e.g., 2 minutes or less) when exposed to body fluids. Examples of dissolvable coating materials include types of material that dissolve upon exposure to body fluids, specific types being used in the field of dissolvable coatings used on cardiac electrodes. The dissolvable materials are described, for example in the following United States patent documents, the entire contents of which are incorporated herein by reference: U.S. Pat. Nos. 4,827,940; 6,304,786; and 7,218,971.

Referring to FIG. 4, distal end 144 of an expansion member includes extension 170, which is an elongate, straight, curved, and optionally sharp, or to otherwise shaped, lead or frictional surface that can be contacted with or inserted into tissue at a surgical site. Extension 170, when in contact with tissue, can prevent movement of distal end 144 relative to the tissue, to secure the position of distal end 144 during a surgical procedure. In use, extension 170, including coating 172, is placed to contact or penetrate tissue. Fluid from the tissue causes coating 172 to dissolve or to be absorbed, leaving an uncotated extension 170 in contact with the tissue.

FIGS. 5A, 5B, 5C, and 5D show an example of an expansion member that can be expanded (and retracted) by use of an electroactive polymer, inside of a patient, to retract tissue. The expansion member can be placed within a patient, optionally by use of a separate introducer. The expansion member can be placed in a patient in a closed configuration (and an optional introducer removed). Once placed, voltage can be applied to the expansion member to cause the expansion member to expand within the patient to cause retraction of tissue, especially when placed vaginally or transabdominally to access a posterior pelvic location.

An electroactive polymer is capable of changing shape upon application of an electric field to the electroactive polymer. According to this embodiment of an expansion member, an electroactive polymer can be applied to or placed into contact with one or more surface of an expansion member, in a manner that exposure of the electroactive polymer to an electric field (e.g., current or voltage) causes the expansion member to change shape between a rolled or "closed" configuration, and an unrolled or "opened" configuration. A application of and removal of current or voltage to the electroactive polymer will cause the expansion member to transition between opened and closed configurations. During such transformation from a closed to an opened configuration the expansion member piece can produce a force against tissue that is sufficient to retract the tissue.

Referring to FIGS. 5A, 5B, 5C, and 5D (all side perspective views), expansion member 240 includes expansion member piece 260 and optional introducer piece 262. Expansion member piece 260 includes proximal end 242, distal end 244, sidewalls 246 extending between proximal end 242 and distal end 244, and electric lead or leads 250 extending away from proximal end 242. Sidewalls 246 are in the form of an expandable tube made, for example, of a sheet of continuous expandable material such as a coiled or spiral sheet of thin metal or plastic. Introducer piece 262 is an elongate fixed or expandable tube or other structure that can be introduced into a surgical incision at an abdomen or vagina. Introducer piece 262 has a size and a shape that allow expansion member piece 260 to fit within the introducer piece 262, when expansion member piece 260 is in a rolled or closed configuration. Introducer piece 262 can be first introduced into a surgical incision (see FIG. 5B). Expansion member piece 260 in a closed configuration can be introduced into introducer piece 262, and introducer piece 262 can be removed from the patient (see FIG. 5C), leaving expansion member piece 260 in the incision (see FIG. 5D).

An electroactive polymer is located on the expansion member piece 260 at locations of the surface (inner surface, outer surface, or both) such that when the electroactive polymer is exposed to or stimulated by an electric field, e.g., a current or voltage is applied to (or removed from) the electroactive polymer, the electroactive polymer changes shape; the expansion member piece 260 changes shape in response to the electroactive polymer changing shape. In use, application or removal of a current or voltage, to the electroactive polymer or other structure (e.g., an electrode) of expansion member piece 260, can transform the shape of expansion member piece 260 from a rolled up or closed form as shown in FIGS. 5A, 5B, and 5C, to an opened or unrolled form as shown at FIG. 5D. During expansion from the closed form to the opened form, expansion member piece 260 can produce sufficient force against tissue to retract the tissue and create an inner opening along a length of expansion member piece 260 that allows access to a surgical site.

In use, expansion member piece 260 can be used alone or in combination with introducer piece 262. When used alone, expansion member piece 260 can be inserted into a patient incision (e.g., an abdominal or vaginal) in the closed configuration and then expanded into the opened configuration to retract tissue. A surgeon can perform a surgical procedure in the pelvic region, such as an SCP procedure with the expansion member placed in the incision and in the opened configuration to retract tissue and allow access to a surgical site. After the surgical to procedure is completed, the expansion member piece can be placed in the closed configuration (by application of or removal of an electric current or voltage) and then removed. The electroactive polymer may be activated or deactivated, e.g., current or voltage can be applied or removed, to cause the expansion member piece to change between the closed and the opened, then the closed, configurations.

When optional introducer piece 262 is used in combination with expansion member piece 260, introducer piece 262 can be first introduced into a surgical incision such as a vaginal or abdominal incision. A distal end of introducer piece 262 can be placed at a desired surgical site such as at a region of sacral anatomy. Expansion member piece 260 in a closed configuration, can be introduced into introducer piece 262 so that distal end 244 is placed at the surgical site, e.g., a region of sacral anatomy. Introducer piece 262 can be removed from the patient, leaving expansion member piece 260 in the incision, which can be expanded to an opened configuration. A surgical procedure can be performed, and expansion member piece 260 can be removed, optionally by first transforming expansion member piece 260 to the closed configuration.

FIGS. 6A, 6B, 6C, 7A, 7B, 7C, 7D, and 7E illustrate examples of expansion member systems that include an introducer piece and an expansion member piece (as do FIGS. 5A, 5B, 5C, and 5d). Referring to FIGS. 6A, 6B, 6C, 7A, 7B, 7C, 7D, and 7E, the expansion member piece includes a generally rigid tube or other form of expansion member, for retracting tissue such as by maintaining the position of tissue that is first retracted using the introducer piece. The introducer piece includes a proximal end, a distal end, and two opposing side sections (e.g., sidewalls, such as blades, or other moveable surfaces). At FIGS. 6A, 6B, 6C, side sections are in the form of two generally flat blades (sidewalls) joined together at their opposing edges by a flexible plastic (e.g., polyethylene, polypropylene, or other polyolefin) or fiber (e.g., a continuous fabric, woven, non-woven, knit, etc.) connective sheet or film material (sheathing, membrane) that can be folded between or adjacent to the blades to allow the blades to take on a "butted," "closed," or "collapsed" state. See FIG. 6A. The blades, which may be substantially flat (as illustrated), or somewhat curved, have lengths between the proximal and distal ends that can provide an inner opening or workspace between a vaginal introitus or abdominal incision, and a posterior pelvic region, including a sacrum and sacral promontory.

Referring to FIGS. 6A, 6B, and 6C, exemplary introducer piece 300 can be useful in a transvaginal or transabdominal sacrocolpopexy procedure to allow fixation of an implant to a region of sacral anatomy such as an anterior longitudinal ligament of a sacrum. The blades can be introduced into a vaginal introitus and through a posterior vaginal incision of open vaginal cuff, into the peritoneal cavity, to locate and identify a sacral promontory by tactile feedback. Alternately, the blades can be introduced into an abdominal incision and advanced to a posterior location of a pelvic region (e.g., into the peritoneal cavity), to locate and identify a sacral promontory by tactile feedback. Once the promontory is located, the collapsed set of opposing blades can be separated and expanded at the proximal end to allow insertion of a separate expansion member piece, such as a self-lit retractor in the shape of an elongate member (e.g., rigid circular or rectangular tube). As the expansion member piece is inserted and pushed distally, farther into the peritoneal cavity toward the sacrum, the opposing retractor blades of the introducer piece are driven apart and the flexible connective material is extended between the opposing blades. The action can have the effect of pushing small and large bowel away from the sacrum to create a bowel-free access channel from the introitus to the sacral promontory.

Referring to FIGS. 6A, 6B, and 6C, introducer piece 300 includes proximal end 308, distal end 310, opposing sidewalls or blades 302, and membrane 304 connecting opposing upper and lower edges of opposing blades 302. Distal end 310 includes a slant or taper 311 designed to match a shape of a sacrum when introducer piece 300 is placed transvaginally or transabdominally within a vaginal incision or an abdominal incision, respectively, with distal end 310 located at a region of a sacrum. Expansion member piece 312 is in the form of a substantially rigid and cylindrical tube that includes proximal end 316, distal end 318, opposing sidewalls 322 (of the tube), optional top or bottom openings (not shown), light 314 along a length toward distal end 318, and inner opening or channel 315. Distal end 318 also includes a slant or taper 320 designed to match a shape of a sacrum when expansion member piece 312 is placed transvaginally or transabdominally between a vaginal incision or an abdominal incision, respectively, with distal end 318 located at a region of a sacrum.

In use, introducer piece 300 can be first introduced into a surgical incision such as a vaginal or abdominal incision. With blades 302 butted together and membrane 304 folded between or adjacent to blades 302, distal end 310 can be introduced through a surgical incision and advanced toward and placed at a desired surgical site such as at a region of a sacrum. Distal end 310 can be used to deflect the sigmoid colon of the sacral promontory and then become located over the sacral promontory to provide access to the sacral promontory. With introducer piece 300 placed as desired, expansion member piece 316 can be inserted into proximal end 308 between blades 302 and advanced distally toward distal end 310. The advancement causes blades 302 to separate and introducer piece 300 to expand and open with movement of blades 302 apart from each other and unfolding of membranes 304. Expansion member piece 312 can be advanced to place distal end 318 at a surgical location such as to access a region of a sacrum and a sacral promontory. Expansion member 312, between proximal end 316 and distal end 318, includes inner opening or channel 315 leading to bowel-free access to a sacral promontory at distal end 318. A surgical procedure can be performed through inner opening 315 of expansion member piece 312, optionally after removing introducer piece 300 from the incision.

FIGS. 7A, 7B, 7C, 7D, and 7E illustrate another example of an expansion member system that includes an expansion member piece 312 (retractor or retractor component or tube) and introducer piece 300. In this embodiment, introducer piece 300 includes three separable items or pieces including a tubular membrane pouch 305 (for producing dilation) and two separable (e.g., malleable) blades 302. Tubular membrane pouch 305 is a flexible fabric or polymeric tube that can fit (e.g., loosely) around expansion member piece 312, and that can be alternately folded or collapsed then opened or expanded by inserting blades 302 into an inner channel of membrane pouch 305. Membrane pouch 305 may be made of, e.g., a flexible polymer or fabric (woven, non-woven, knit, etc.) material such as polyethylene, polyurethane, silicone, or a textile material and can optionally include pockets on two sides to house blades 302. Membrane pouch 305 can be flexible to allow folding between or adjacent to the blades. Blades 302 can fit within the membrane pouch 305 along with expansion member piece 312.

Expansion member piece 312 can be as described herein, such as in the form of a clear, transparent, tubular rigid polymeric member having distal end 318, proximal end 316, and a length and sidewalls 322 therebetween, with distal end 318 shaped (angled) for close contact with the sacrum when expansion member piece 312 is placed within a vaginal or abdominal incision. The length of body sidewall 322 extending between proximal end 316 and distal end 318 can provide an inner opening and workspace 315 between a surgical incision at a location of an abdominal incision or a location of a vaginal introitus, and a posterior pelvic region such as a location of a sacrum, sacral promontory, or other sacral anatomy. Expansion member 312 can include an optional lighting feature (not illustrated), for example in the form of a solid optical fiber extending inside of the tube or at an interior of the tube sidewall.

Figure 7A:
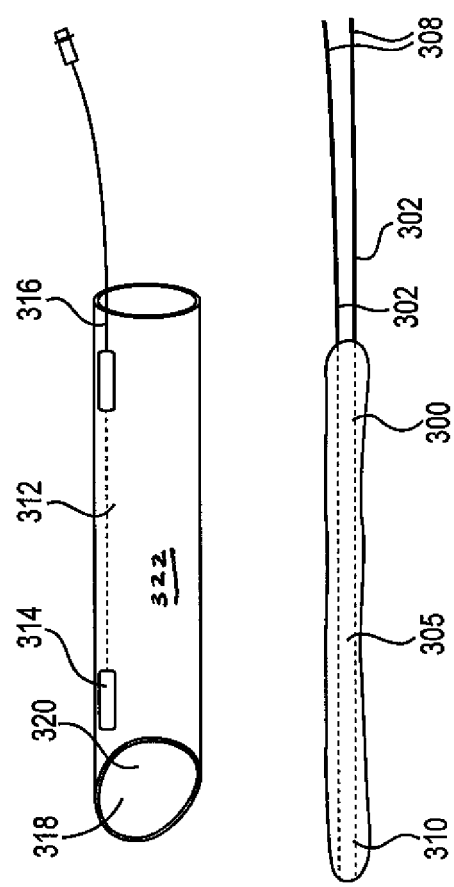
FIGS. 7A and 7B are side views of an expansion member system including an introducer piece and an expansion member piece.
Figure 7B:
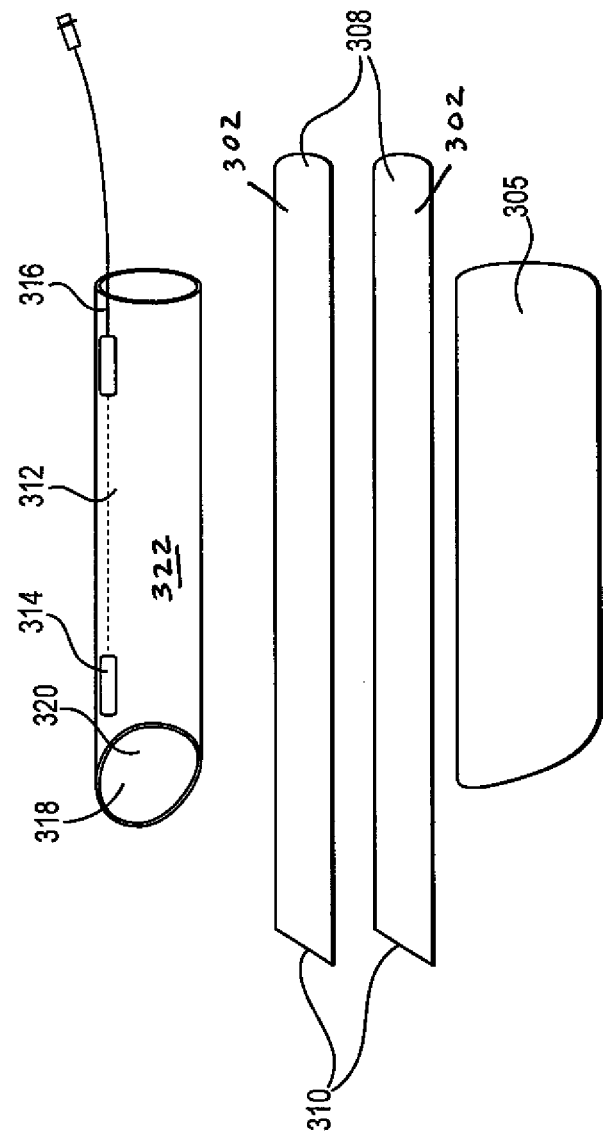
Figure 7E:
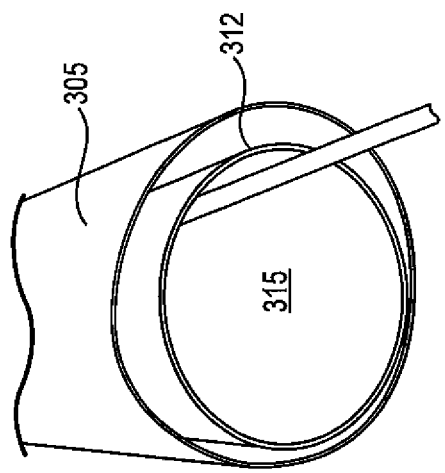
FIGS. 7C, 7D, 7E are end views of the system.
Figure 7D:
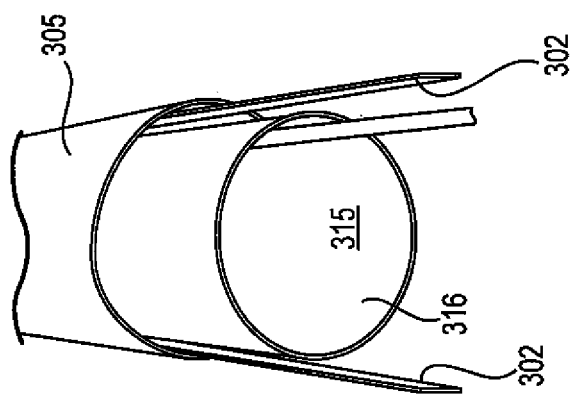
Figure 7C:
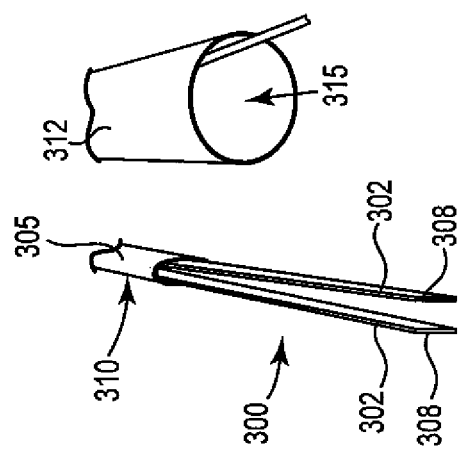

According to specific methods, an introducer piece 300 and an expansion member 312 as illustrated at FIGS. 7A, 7B, and 7C, can be used together by steps that include: inserting and using inserter device 300 (including an assembly of membrane pouch 305 and blades 302) through a surgical incision, with distal end 310 located at a region of sacral anatomy and used to deflect the sigmoid colon; palpating and identifying the sacral promontory; and clearing the adjacent area (making sure no bowel interferes with access). Once clean contact with the sacral promontory is established, the dilating component (membrane pouch 305) is expanded by separating the malleable blades at proximal end 308, which is external to the patient, to allow insertion of the retraction tube (expansion member piece 312) into membrane pouch 305. The expansion member piece 312 is advanced slowly into the central inner lumen of membrane pouch 305, between opposing blades 302, and advanced distally to a region of the sacrum. Leading edge 320 of expansion member piece 312 can be keyed (angled) such that the top edge of the angled distal end sits on top of the promontory for easy identification of the structure. Once expansion member piece 312 has been advanced to a desired distal location, malleable blades 302 can be withdrawn to allow for a less crowded proximal end, for easy access to the workspace and easy introduction of instruments through inner opening 315 of expansion member piece 312.

FIGS. 8A, 8B, 8C, 8D, 8E, 8F, 8G, 8H, and 8I illustrate examples of surgical tools in the form of "blunt dissection devices" 350, which include proximal end 352, shaft 354, distal end 356, and handle 358 at proximal end 352. A distal end 356 includes a blunt dissection feature or surface such as a blunt (e.g., rounded, dull, or slightly sharpened) distal edge or distal surface 362 of a paddle 360. Paddle 360 or a surface thereof can be used to contact tissue (e.g., at or proximal to a region of sacral anatomy) to cause dissection or otherwise move or retract tissue by manipulation of handle 358 at proximal end 352. The blunt dissection surface may include one or a combination of a rigid, curved or flat paddle, and an optional expandable structure or surface such as a balloon, expandable metal cage, or other surface moveable relative to a surface of the paddle. Alternate embodiments of a blunt dissection surface or paddle may include one or more of the following optional features: a cutting feature such as a blade or pressurized air, an irrigation feature, a suction feature, a lighting feature (e.g., light 112 and battery 110 of certain figures), or an ultrasonic energy or other vibration feature.

Figure 8A:
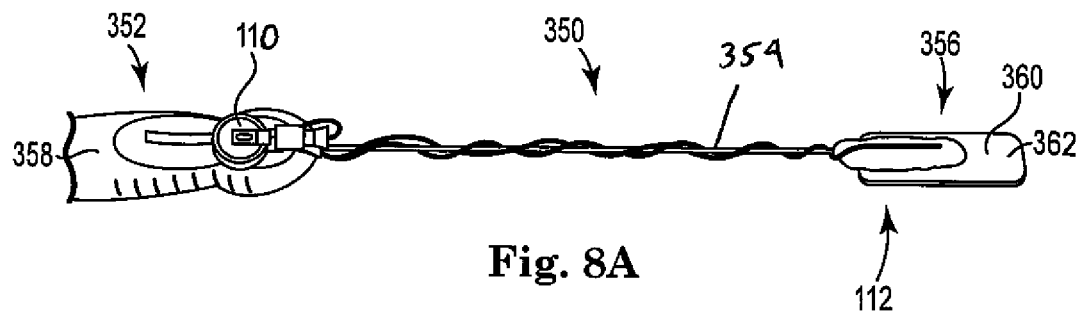
FIG. 8A is a side perspective view of a dissection device.
Figure 8B:
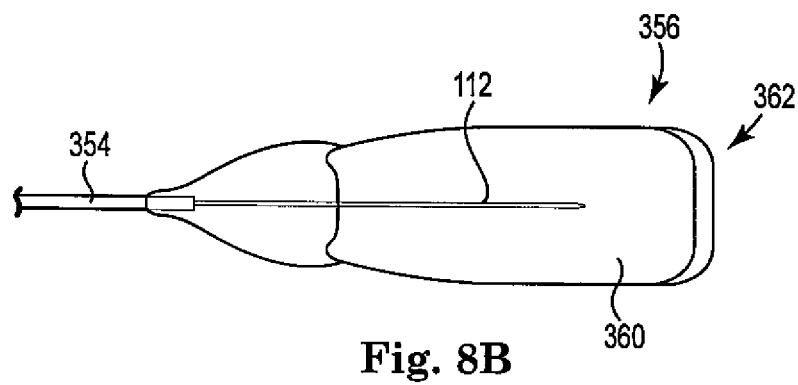
FIGS. 8B and 8C are top and side views of a distal end of a dissection device.
Figure 8C:
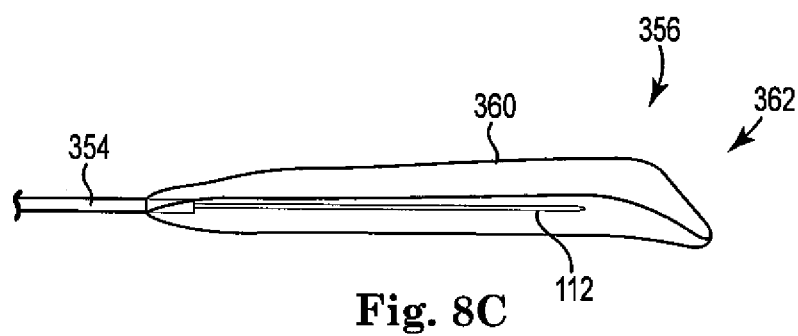

Referring to FIGS. 8A, 8B, and 8C, blunt dissection device 350 includes proximal end 352, shaft 354, distal end 356, and handle 358 at proximal end 352. Paddle 360 may be flat (FIG. 8A) or curved about a longitudinal axis (FIG. 8C). Light 112 is energized by battery 110. Shaft 354 has a low profile or cross section to allow use through a vaginal or abdominal incision, or through an opening in an expansion member, without obstruction a view of a distal surgical site. Shaft 354 may be a straight, rigid metal (e.g., stainless steel, titanium) or rigid plastic shaft of small cross-sectional dimension (e.g., diameter), such as having a diameter of 1 to 10 millimeters, e.g., 2 to 6 millimeters.

Figure 8D:
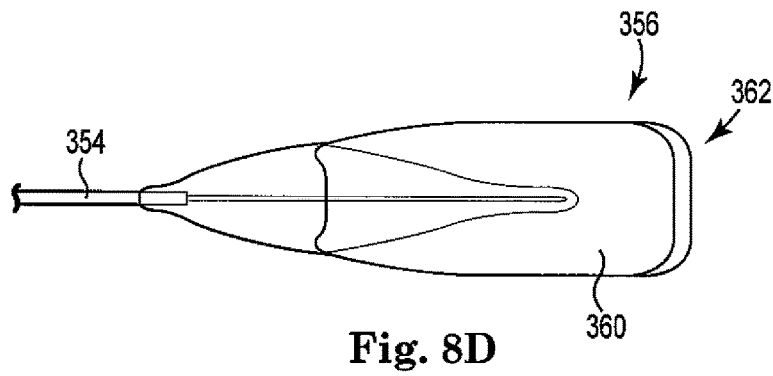
FIGS. 8D, 8G, and 8H are top views of distal ends of dissection devices.
Figure 8E:
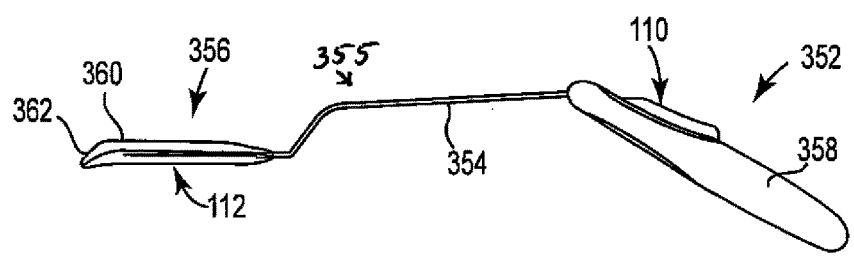
FIG. 8E is a side view of a dissection device.

Blunt dissection device 350 of FIGS. 8D and 8E is similar to device 350 of FIG. 8A, except that shaft 354 includes bends or curves toward distal end 356 to stagger or offset the position of paddle 360 relative to a proximal portion (355) of shaft 354. Paddle 360 is parallel to proximal portion 355 of shaft 354, but offset. Also, handle 358 is angled (e.g., at an angle in a range from 10 to 80 degrees, such as from 30 to 60 degrees) relative to proximal portion 355 of shaft 354. The offset paddle and the angled handle can be featured alone or separately to allow to manipulation of tissue by paddle 360 with open viewing of an adjacent surgical site.

Figure 8F:
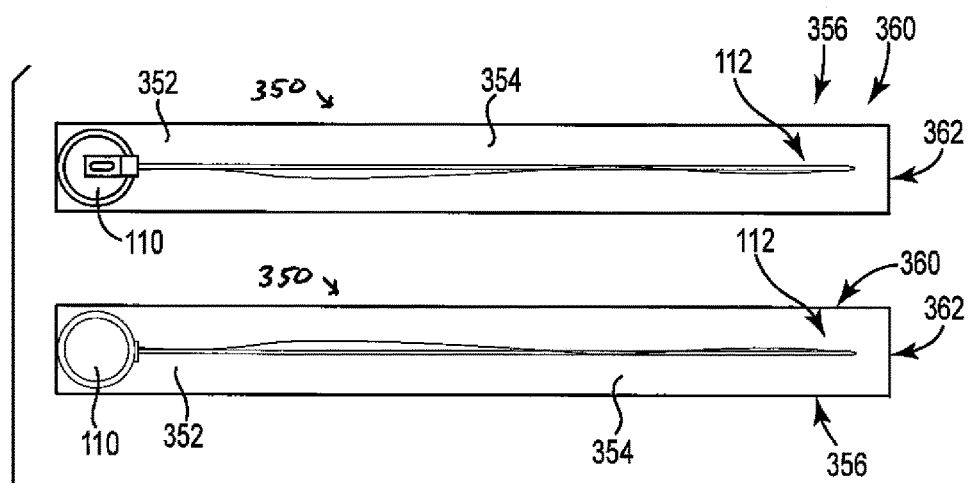
FIG. 8F is a top and bottom view of a dissection device.

FIG. 8F shows a top view and a bottom view of blunt dissection device 350, which is an elongate flat blade having other features as presented.

Figure 8G:
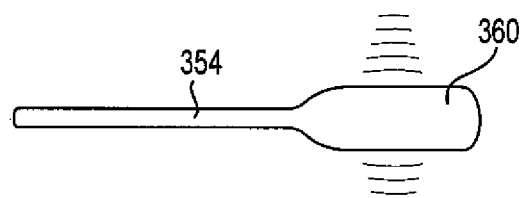

Referring in particular to FIG. 8G, ultrasonic energy can emanate from paddle 360, which can vibrates either laterally (as illustrated) or longitudinally.

Figure 8H:
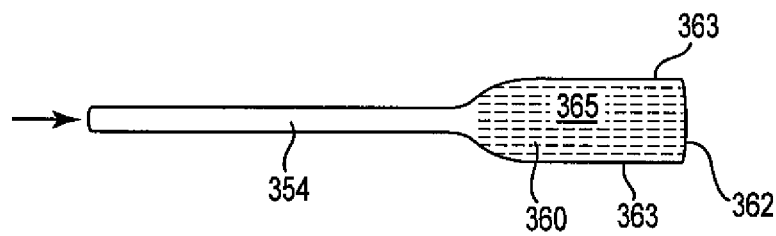

Referring in particular to FIG. 8H, pressurized air can flow along or through shaft 354 and be ejected through orifices (not shown) located on paddle 360, either at a flat or curved surface 365 of paddle 360, or at an edge such as distal edge 362 or at one or both of side edges 363. Ultrasonic energy can emanate from paddle 360, which can vibrate laterally (as illustrated), longitudinally, or both.

Figure 8I:
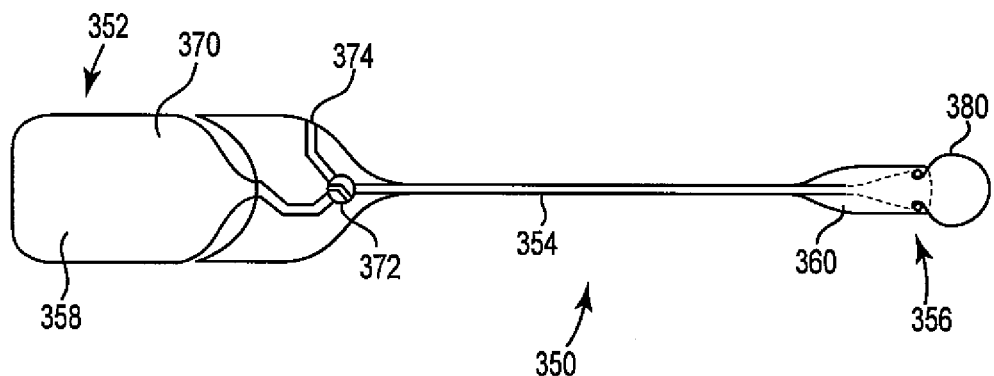
FIG. 8I is a top view of a dissection device.

Referring to FIG. 8I, device 350 includes proximal end 352, shaft 354, distal end 356, and handle 358. Distal end 356 includes paddle 360, which includes expandable surface (e.g., balloon) 380. Expandable surface 380 can be located at a surface or distal or side edge of paddle 360. Handle 358 includes moveable or flexible bellows or flexible air reservoir or chamber 370, which can be compressed to force air through valve 372 along shaft 354 and into an interior space of expandable surface (e.g., balloon) 380. To deflate expandable surface 380, a switch at valve 372 can be moved to connect the interior space of expandable surface 380 to outlet 374.

The figures illustrate embodiments of blunt dissection devices 350 that can include optional features such as an expandable structure (e.g., balloon 380), paddles curved laterally (e.g., about a lengthwise direction, see FIGS. 8B and 8C), a longitudinal axis of shaft 354 aligned with a longitudinal axis of handle 358, or a longitudinal axis of shaft 354 bent relative to a longitudinal axis of handle 358 (see FIG. 8E). A preferred flat or curved (laterally) paddle may have an elongate but narrow size and shape, such as about a width (a major dimension of a paddle extending in a direction perpendicular to a length) of a finger (e.g., 1.5 to 2.5 centimeters) or somewhat wider (e.g., from 1.5 to 3 or 4 centimeters). A preferred expandable structure may be a fluid-inflatable (e.g., air, carbon dioxide, nitrogen, etc.) balloon, which in use can be placed in contact with tissue and expanded to adjust the position of tissue, e.g., retract the tissue during a surgical procedure. The distal end can also optionally and preferably include a light for better viewing of a to surgical space by a surgeon. The dissection tool can be used in combination with a rectal probe 580 (see FIG. 8J).

Figure 8J:
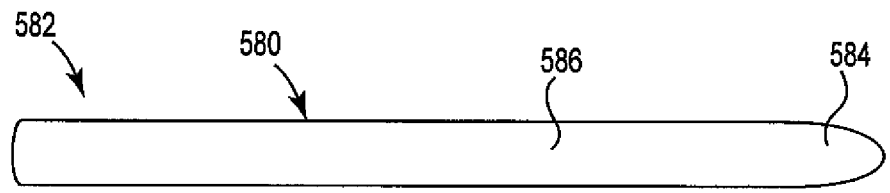
FIG. 8J is a side view of a rectal probe.
Figure 9:
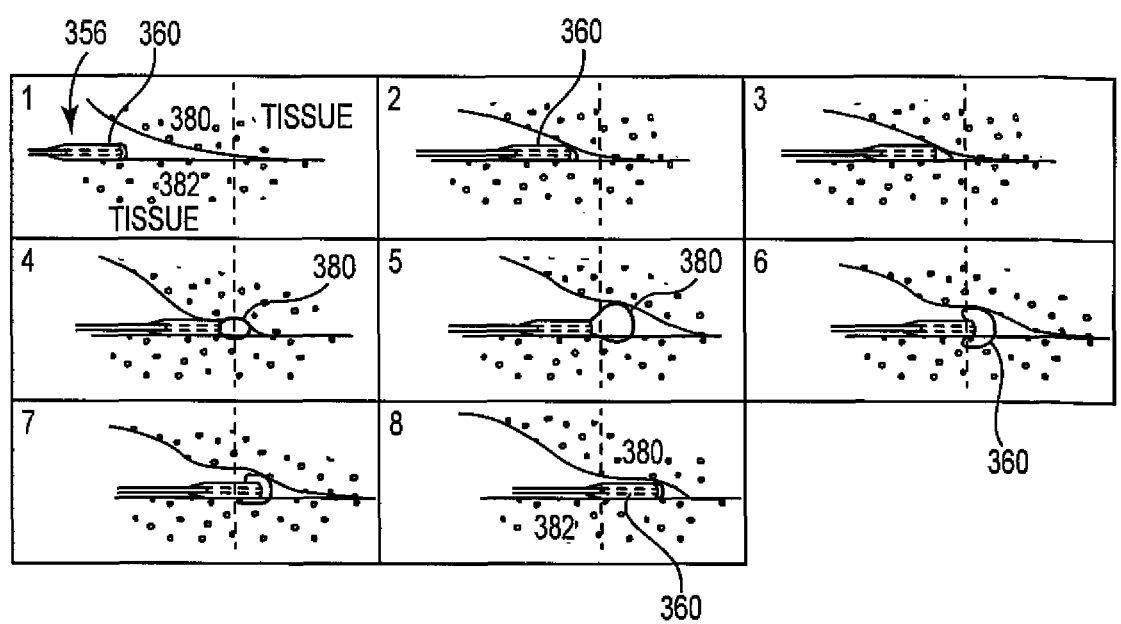
FIG. 9 is a series of panels illustrating steps of using a blunt dissection device to retract or dissect tissue.

FIG. 9 includes panels that illustrates a series of steps for using a blunt dissection tool 350, such as the one shown at FIG. 8I that includes an expandable surface (e.g., balloon) 380 as part of paddle 356. At panel 1, FIG. 9 shows a distal end 356 and paddle 360 advancing distally between two opposing tissue surfaces 380 and 382. Panels 2 and 3 show paddle 356 progressing distally between the tissue surfaces. At panel 4, balloon 380 begins expansion and at panel 5 expansion continues in a manner such that the expanding surface of balloon 380 presses against the tissue surfaces to increase separation between the tissue surfaces. At FIG. 6, tool 350 is advanced farther distally (in the direction of the arrow), with balloon 380 in an expanded configuration. At FIGS. 7 and 8 the size of balloon 380 is reduced, e.g., by deflation, and at panel 8 tool 350 can be advanced farther distally with balloon 380 in a deflated configuration. Subsequently, balloon 380 can be re-inflated (as at FIGS. 4 and 5) and then steps of balloon inflation, distal advancement of tool 350, deflation, etc., can be repeated.

FIG. 8J shows rectal probe 580 having proximal end 582, distal end 584 with a rounded bulbous tip, and shaft 586 extending therebetween. Elongate shaft 586 is substantially straight and includes a substantially circular cross section and a relatively smooth outer surface. Shaft 586 can be made of a substantially rigid material such as plastic, metal, or transparent or translucent plastic. Shaft 586 can contain a light source and may be made of a clear or transparent material to produce illumination when placed in a body lumen such as a rectum or colon. According to methods of using the expansion members of the invention, for use in treating a pelvic condition, a rectal probe 580 can be inserted into a rectum, and illuminated.

Devices as described and illustrated (referred sometimes to interchangeably as "expansion members," "tubes," or "retractors") can be used and useful by a method of inserting the device into a surgical incision, for example a transvaginal or abdominal incision, and moving, retracting, or expanding tissue to provide access to desired anatomy. For performing an SCP or other procedure, a tube or retractor can be placed transvaginally or transabdominally, e.g., in a non-expanded, closed, or collapsed state. The expansion member can then be expanded while in place in the patient incision, e.g., transvaginally or transabdominally, to create access through an inner opening of the expansion member to desired anatomy such as the posterior of a pelvic region, e.g., to gain access to a region of sacral anatomy. The expansion member creates an inner opening or workspace extending between a vaginal introitus or an abdominal incision and a region of sacral anatomy, such as an anterior longitudinal ligament. A surgeon can perform a surgical procedure by use of the access, which provides working space to pelvic anatomy such as the sacrum.

The method can optionally also involve a tool, multi-functional tool, implant, adjustable implant, anchor, or other device or method, e.g., as described at Applicant's co-pending International Patent Application number PCT/US2010/062577, filed Dec. 30, 2010, the entirety of which is incorporated by reference.

As presented, an expansion member or dissection tool as described can include features and structures (e.g., fiber optics) to allow viewing or illumination of a surgical site. Illumination can be accomplished by any of various lighting techniques and structures. If a structural component of an expansion member or dissection tool is made of a plastic or polymeric light-conductive material, light can be transmitted through that material from a proximal end to a distal end at the surgical site. Alternately, a fiber optic cable can be incorporated into a length of the device, extending from a proximal to or toward a distal end, to allow light to be transmitted from the proximal end to the distal end. Light could alternately be generated and shone from the distal end.

Tools and devices as described can be made from any suitable material or combination of materials. Examples include any material save for less than 24 hour contact with tissue, such as stainless steel, nitinol, polycarbonate, polypropylene, polyethylene, fluoropolymer, PET, polyurethane, silicone, polysulphone, and ultem. Any structure of an expansion member, retractor, tube, dissection tool, or other identified component may be capable of conducting light between a proximal and distal end, or alternately one or more fiber optics cable may be incorporated into an expansion member, retractor, tube, or component thereof, to provide lighting.

Implants, their various components, structures, features, materials and methods may have a number of suitable configurations as shown and described in the previously-incorporated references, or as described herein. Various methods and tools for introducing, deploying, anchoring and manipulating implants to treat prolapse or another pelvic conditions, as disclosed in the previously-incorporated references, are envisioned for use with the present invention as well as those methods and tools identified and described herein.

Also according to embodiments of the methods, implants, tools, and devices described herein, any of the described tools can be used for placing any desired pelvic implant in a male or a female patient, and for any of a large variety of conditions, such as a pelvic condition. The implant can include any structural features useful for such treatment, including any desired size, shape, and optional features such as adjustability and anchoring systems. Any of these features may be previously known, future developed, described herein, or described in documents incorporated herein, for any particular implant and method. For example, some figures and discussions include examples of features of "anchors" (e.g., soft tissue or bone anchors, as these terms are generically and inclusively used) that can be useful according to the methods of placing a surgical implant. An implant that includes or is otherwise secured by any of the anchors described can be useful to treat a pelvic condition in a male or a female patient; as a single and non-limiting example, an implant that includes or uses an anchor as described can be used in a transvaginal or transabdominal SCP procedure to provide support to a vaginal cuff, through an implant that includes the anchor, the anchor being attached at a region of sacral anatomy such as a sacral ligament (e.g., anterior longitudinal ligament, a.k.a. the "anterior ligament" or "longitudinal ligament").

Various devices and methods described herein are advantageous because they facilitate reduction of total procedural time needed to treat a pelvic condition.

The various systems, apparatus, and methods detailed herein are envisioned for use with certain known implant and repair systems (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261, WO 2007/097994, WO 2007/149348, and U.S. Patent Publication Nos. 2002/151762, 2010-0174134, 2010-0298630, and 2002/147382. Accordingly, the above-identified disclosures are fully incorporated herein by reference in their entirety.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A medical apparatus for a sacrocolpopoxy, the medical apparatus comprising:
   an expansion member including a tube, the tube having a
      distal end defining a distal end opening, and a proximal end defining a proximal end opening, the tube defining a lumen extending between the distal end opening and the proximal end opening, the distal end including a slant such that the expansion member has a first side and an opposing second side in which the first side has an overall length different than an overall length of the second side; and an introducer configured to be inserted into a body of a patient via a vaginal or abdominal incision, and advanced to a region of a sacrum, the introducer being a device that is physically separate from the expansion member, the introducer including a first panel, a second panel, and a flexible member connected to the first panel and the second panel at opposing upper and lower edges of the first panel and the second panel, the introducer having a collapsed configuration in which the first panel is disposed on top of the second panel with the flexible member folded between the first panel and the second panel, and an expanded configuration in which the first panel is disposed away from the second panel, the expansion member is configured to be inserted between the first panel and the second panel when the introducer is in the collapsed configuration to move the introducer from the collapsed configuration to the expanded configuration, wherein the expansion member, when inserted between the first panel and the second panel, is configured to drive the first panel and the second panel away from each other with the flexible member extending between the first panel and the second panel.

2. The medical apparatus of claim 1, wherein each of the first panel and the second panel is flat.

3. The medical apparatus of claim 1, wherein the tube is cylindrical.

4. The medical apparatus of claim 1, wherein the expansion member includes a light along a length towards the distal end of the expansion member.

5. The medical apparatus of claim 1, wherein the flexible member includes a flexible plastic material.

6. The medical apparatus of claim 1, wherein the flexible member includes a fiber sheet material.

7. The medical apparatus of claim 1, wherein the introducer is configured to be inserted into the body of the patient via the abdominal incision when the introducer is in the collapsed configuration.

8. The medical apparatus of claim 1, wherein a distal end of the introducer is configured to deflect a sigmoid colon of a sacral promontory and move to a location over the sacral promontory to provide access to the sacral promontory.

9. The medical apparatus of claim 1, wherein the medical apparatus is configured to push a bowel away from the sacrum to create a bowel-free access channel from an introitus to a sacral promontory when the introducer is moved from the collapsed configuration to the expanded configuration.

10. The medical apparatus of claim 1, wherein the slant includes a taper configured to match a shape of the sacrum of the patient.

* * * * *